United States Patent
Strömberg et al.

(10) Patent No.: US 9,463,200 B2
(45) Date of Patent: Oct. 11, 2016

(54) CELL-PENETRATING OLIGONUCLEOTIDES

(71) Applicant: Oligomer Sciences AB, Djursholm (SE)

(72) Inventors: Roger Strömberg, Hägersten (SE);
Dmytro Honcharenko, Uppsala (SE);
Stefan Milton, Nybro (SE)

(73) Assignee: OLIGOMER SCIENCES AB, Djursholm (SE)

( * ) Notice: Subject to any disclaimer, the term of this patent is extended or adjusted under 35 U.S.C. 154(b) by 0 days.

(21) Appl. No.: 14/769,997

(22) PCT Filed: Feb. 28, 2014

(86) PCT No.: PCT/EP2014/053964
§ 371 (c)(1),
(2) Date: Aug. 24, 2015

(87) PCT Pub. No.: WO2014/131892
PCT Pub. Date: Sep. 4, 2014

(65) Prior Publication Data
US 2016/0008389 A1 Jan. 14, 2016

Related U.S. Application Data

(60) Provisional application No. 61/770,464, filed on Feb. 28, 2013.

(30) Foreign Application Priority Data

Feb. 28, 2013 (SE) ...................... 1350228

(51) Int. Cl.
C07H 21/02 (2006.01)
C07H 21/04 (2006.01)
A61K 31/70 (2006.01)
A61K 31/712 (2006.01)
C12N 15/113 (2010.01)
C07H 19/067 (2006.01)
C07H 19/167 (2006.01)
C12N 5/00 (2006.01)

(52) U.S. Cl.
CPC ........... A61K 31/712 (2013.01); C07H 19/067 (2013.01); C07H 19/167 (2013.01); C07H 21/02 (2013.01); C12N 15/113 (2013.01); C12N 2310/11 (2013.01); C12N 2310/32 (2013.01)

(58) Field of Classification Search
None
See application file for complete search history.

(56) References Cited

U.S. PATENT DOCUMENTS 5,466,786 A 11/1995 Buhr et al.
5,792,847 A 8/1998 Buhr et al.

FOREIGN PATENT DOCUMENTS

WO 2010048585 10/2010
WO 2011139911 11/2011

OTHER PUBLICATIONS

Crooke, S. T. Annu. Rev. Med., 2004, 55, 61-95.
Crooke, S. T. Curr. Mol. Med. 2004, 4, 465-487.
Bauman J, et al. Oligonucleotides, 2009, 19, 1-13.
Moser E. Hum Genet 1984, 66, 17-40.
Emery AE. Lancet 2002, 359, 687-695.
S. M. Freier, K. H. Altmann, Nucleic Acids Res 1997, 25, 4429.
M. Egli, et al. Biochemistry 2005, 44, 9045.
E. A. Lesnik, et al. Biochemistry 1993, 32, 7832.
M. Grotli, et al.Tetrahedron 1999, 55, 4299.
S. Milton, et al. Eur. J. Org. Chem., 2012, 539-543.
H. Ozaki, S. et al. Nucleosides, Nucleotides Nucleic Acids 2009, 28, 943-952.
Gary D. Gray, et al. Biochemical Pharmacology, 1997, 53, 1465-1476.
Zhong, M and Strobel, S. A. J. Org. Chem. 2008, 73, 603-611.
Prakash T. P. et al. J. Med. Chem. 2008, 51, 2766-2776.
Kachalova, A., et al. Org. Biomol. Chem., 2004, 2, 2793-2797.
Honcharenko et al, RSC Advances 2012, 2(33): 12949.
Milton et al, Eur J Org Chem 2013, 31:7184-7192.
International Search Report and Written Opinion of the International Searching Authority, or the Declaration, mailed Apr. 29, 2014, in PCT/EP2014/053964.

Primary Examiner — Sean McGarry
(74) Attorney, Agent, or Firm — Dilworth IP LLC

(57) ABSTRACT

The present invention relates to modified oligonucleotides of 5-50 nucleotide residues, wherein at least 25% of the nucleotides are independently modified at the 2' position to comprise the structure of formula (I), wherein base is a purine or pyrimidine moiety; and $R^1$, $R^2$, $R^3$, $R^4$, p and q are as defined in the description. The modified oligonucleotides comprising said structures are useful as medicaments for enhancement of drug uptake in oligonucleotide based therapy in humans and animals.

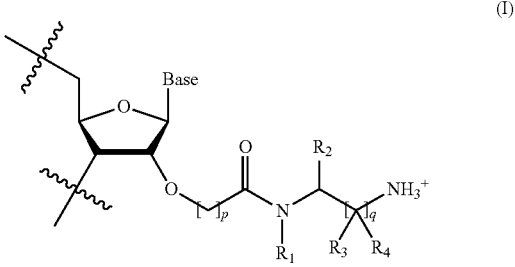

(I)

15 Claims, 4 Drawing Sheets

```
                           SEQUENCE LISTING

<160> NUMBER OF SEQ ID NOS: 11

<210> SEQ ID NO 1
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: 2'-O-AECM
<220> FEATURE:
<221> NAME/KEY: misc_feature
<222> LOCATION: (8)..(9)
<223> OTHER INFORMATION: 2'-O-AECM
<220> FEATURE:
<221> NAME/KEY: misc_feature
<222> LOCATION: (13)..(13)
<223> OTHER INFORMATION: 2'-O-AECM
<220> FEATURE:
<221> NAME/KEY: misc_feature
<222> LOCATION: (16)..(16)
<223> OTHER INFORMATION: 2'-O-AECM

<400> SEQUENCE: 1
ggaccggaag gtacgag                                                    17

<210> SEQ ID NO 2
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 2
ggaccggaag gtacgag                                                    17

<210> SEQ ID NO 3
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(3)
<223> OTHER INFORMATION: 2'-O-AECM
<220> FEATURE:
<221> NAME/KEY: misc_feature
<222> LOCATION: (5)..(7)
<223> OTHER INFORMATION: 2'-O-AECM
<220> FEATURE:
<221> NAME/KEY: misc_feature
<222> LOCATION: (9)..(9)
<223> OTHER INFORMATION: 2'-O-AECM
<220> FEATURE:
<221> NAME/KEY: misc_feature
<222> LOCATION: (11)..(11)
<223> OTHER INFORMATION: 2'-O-AECM
<220> FEATURE:
<221> NAME/KEY: misc_feature
<222> LOCATION: (14)..(14)
```

```
<223> OTHER INFORMATION: 2'-O-AECM

<400> SEQUENCE: 3
gaagaaagag aggagg                                                    16

<210> SEQ ID NO 4
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 4
gaagaaagag aggagg                                                    16

<210> SEQ ID NO 5
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(4)
<223> OTHER INFORMATION: 2'-O-AECM
<220> FEATURE:
<221> NAME/KEY: misc_feature
<222> LOCATION: (6)..(7)
<223> OTHER INFORMATION: 2'-O-AECM
<220> FEATURE:
<221> NAME/KEY: misc_feature
<222> LOCATION: (9)..(9)
<223> OTHER INFORMATION: 2'-O-AECM
<220> FEATURE:
<221> NAME/KEY: misc_feature
<222> LOCATION: (12)..(12)
<223> OTHER INFORMATION: 2'-O-AECM

<400> SEQUENCE: 5
caaagaacac cag                                                       13

<210> SEQ ID NO 6
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 6
caaagaacac cag                                                       13

<210> SEQ ID NO 7
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(12)
<223> OTHER INFORMATION: 2'-O-AECM

<400> SEQUENCE: 7
aaaaaaaaaa aaa                                                       13

<210> SEQ ID NO 8
<211> LENGTH: 13
<212> TYPE: DNA
<213> ORGANISM: Artificial Sequence
```

```
<220> FEATURE:
<223> OTHER INFORMATION: Synthetic oligonucleotide

<400> SEQUENCE: 8
aaaaaaaaaa aaa                                                            13

<210> SEQ ID NO 9
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(10)
<223> OTHER INFORMATION: 2'-O-AECM

<400> SEQUENCE: 9
aaaaaaaaaa                                                                10

<210> SEQ ID NO 10
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 10
aaaaaaaaaa                                                                10

<210> SEQ ID NO 11
<211> LENGTH: 18
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(18)
<223> OTHER INFORMATION: 2'-O-AECM

<400> SEQUENCE: 11
ccucuuaccu caguuaca                                                       18
```

CELL-PENETRATING OLIGONUCLEOTIDES

FIELD OF INVENTION

The present invention relates to the field of molecular biochemistry and medicine, and in particular to oligonucleotides comprising modified nucleotide residues, useful in technologies which rely on complementarity or specificity of oligomer sequences for drug delivery or for direct interference with nucleic acid activity.

BACKGROUND OF THE INVENTION

There has been considerable activity in recent years concerning the design of nucleic acids as diagnostic and therapeutic tools. One aspect of this design relies on the specific attraction of certain oligomer sequences for nucleic acid materials in vivo which mediate disease or tumors. This general approach has often been referred to as "anti-sense" technology. A simplified statement of the general premise is that the administered oligomer is complementary to the DNA or RNA which is associated with, and critical to, the propagation of an infectious organism or a cellular condition such as malignancy. The premise is that the complementarity will permit binding of the oligomer to the target nucleic acid, thus inactivating it from whatever its function might have been, or alter the processing of it to result in alternative product.

Synthetic nucleic acids have been pivotal for the development of life science research, and modified oligonucleotides are developed as a means to treat patients with genetic disease. Most oligonucleotide therapies, including siRNA (short interfering RNA) and antisense technologies (Crooke, S. T. *Annu. Rev. Med.,* 2004, 55, 61-95; Crooke, S. T. *Curr. Mol. Med.* 2004, 4, 465-487), including splice-switching (Bauman J, et al. *Oligonucleotides,* 2009, 19, 1-13), are limited by e.g., lability of oligonucleotides in biological fluids and poor delivery to the site of action. Efficiency in regulation of gene expression is more readily achieved if turnover of the target RNA is obtained. This can occur if native enzymes (e.g., RNAse H for antisense and RISC complex for siRNA) can recognise the relevant oligonucleotide complex. A number of diseases cannot be treated by reduction of a specific RNA as some diseases are caused by production of a mis-spliced RNA. For quite a number of such diseases, the RNA produced can be splice-corrected or splice-switched to produce either the correct RNA or an alternative RNA that gives a protein with functions resembling that of the native protein or having other desired properties. Since degradation of the target RNA is not required or even desired there is on the other hand no limitation in modifications due to a need for recognition by cellular degrading enzymes (e.g., RNase H) which opens up the possibility to use oligonucleotides that give tighter binding and high stability to degradation but that are not recognised by such enzymes. A prototype disease for splice-switching therapy is the devastating Duchenne muscular dystrophy (DMD: Moser E. *Hum Genet* 1984, 66, 17-40; Emery A E. *Lancet* 2002, 359, 687-695).

A number of oligonucleotide modifications have been explored in the development of oligonucleotides for biotechnology or therapy. 2'-O-alkyloligoribonucleotides (S. M. Freier, K. H. Altmann, *Nucleic Acids Res* 1997, 25, 4429) is a class of modification that has rendered interest. To modify the 2'-position has several advantages, including low cost starting materials. Compared to 2'-deoxynucleosides, 2'-F- or 2'-O-alkylnucleosides (having electron withdrawing groups in the 2'-position) pushes the conformational equilibrium in the sugar moiety toward the north (C3'-endo) conformations consistent with the A-form geometry of RNA duplexes, which typically leads to more stable duplexes with the target RNA (M. Egli, et al. *Biochemistry* 2005, 44, 9045). A number of 2'-O-alkyloligoribonucleotide modifications have, as compared to DNA, been shown to give increased stability of duplexes with RNA (E. A. Lesnik, et al. *Biochemistry* 1993, 32, 7832). Recently the 2'-O-carbamoylmethyl (CM) modification has been studied (M. Grotli, et al. *Tetrahedron* 1999, 55, 4299) and it was found interesting not least as potential backbone for artificial nucleases and showed that this is highly resistant to enzymatic degradation (S. Milton, et al. *Eur. J. Org. Chem.,* 2012, 539-543).

A single 2'-O-(N-(aminoethyl)carbamoyl)methyl) (AECM) modification in an oligonucleotide resulted in a substantial decrease in melting point of duplexes (H. Ozaki, S. et al. *Nucleosides, Nucleotides Nucleic Acids* 2009, 28, 943-952). A single AECM modification in a dinucleotide enhanced its stability to nuclease cleavage, and the AECM modification was mentioned as an example of a suitable linker moiety for conjugation to additional substances (U.S. Pat. No. 5,466,786). A favourable nuclease stability of modified oligonucleotides has previously been shown to be in contrast with an efficient cellular uptake of the same (Gary D. Gray, et al. *Biochemical Pharmacology,* 1997, 53, 1465-1476).

SUMMARY OF THE INVENTION

An object of the invention is to provide a modified oligonucleotide with enhanced cellular uptake compared to the corresponding non-modified oligonucleotide.

Other objects of the invention are to provide a method of manufacturing the modified oligonucleotide, and to provide building blocks for manufacturing the modified oligonucleotide.

The inventors have identified that oligonucleotides containing a substantial degree of the 2'-O-(N-(aminoethyl) carbamoyl)methyl (AECM) modification (FIG. 1) and/or structurally related modifications actually exhibits an increase in melting point of duplexes and enhanced cellular uptake of the oligonucleotide, which makes these modifications surprisingly suitable for enhancement of drug uptake into human cells in oligonucleotide based therapy and possibly also as vectors for other drugs.

Preferred embodiments of the invention are provided in the following description and from the appended claims and the itemized listing of preferred embodiments.

BRIEF DESCRIPTION OF THE SEQUENCES

Figure 1:
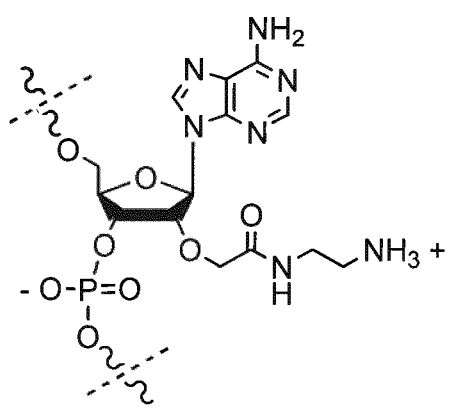
FIG. 1 shows the structure of the 2'-O-(N-(aminoethyl) carbamoyl)methyl (AECM) modification.

The sequences of representative and tested oligonucleotides are as follows:

| SEQ ID NO | | Nucleotide sequence |
|---|---|---|
| SEQ ID NO 1 | (O1) | GGaCCGGaaGGTaCGaG |
| SEQ ID NO 2 | (dO1) | GGACCGGAAGGTACGAG |
| SEQ ID NO 3 | (O2) | GaaGaaaGaGaGGaGG |
| SEQ ID NO 4 | (dO2) | GAAGAAAGAGAGGAGG |
| SEQ ID NO 5 | (O3) | CaaaGaaCaCCaG |
| SEQ ID NO 6 | (dO3) | CAAAGAACACCAG |
| SEQ ID NO 7 | (O4) | aaaaaaaaaaaaA |
| SEQ ID NO 8 | (dO4) | AAAAAAAAAAAAA |
| SEQ ID NO 9 | (O5) | aaaaaaaaaa |
| SEQ ID NO 10 | (dO5) | AAAAAAAAAA |
| SEQ ID NO 11 | (O6) | ccucuuaccucaguuaca |

In the sequences, "a" represents 2'-O-AECM-adenosine, "c" represents 2'-O-AECM-cytidine, "g" represents 2'-O-AECM-guanosine, "u" represents 2'-O-AECM-uridine, and "A", "C", "G" and "T" represent its respective 2'-deoxyribonucleotide.

ITEMIZED LISTING OF PREFERRED EMBODIMENTS

1. A modified oligonucleotide of 5-50 nucleotide residues, wherein at least 25% of the nucleotides are independently modified at the 2' position to comprise the structure of formula I:

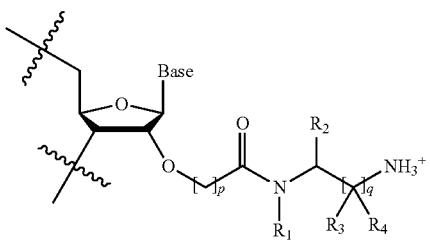

I wherein
Base is a purine or pyrimidine moiety;
$R^1$ and $R^2$ are independently selected from hydrogen and $C_1$-$C_3$ alkyl;
$R^3$ is selected from hydrogen and $C_1$-$C_6$ alkyl;
$R^4$ is selected from hydrogen and $C_1$-$C_{16}$ alkyl;
p=1 or 2; and
q=1 or 2.

2. The modified oligonucleotide according to embodiment 1, wherein at least 50%, preferably at least 80%, of the nucleotides of the oligonucleotide are independently modified at the 2' position to comprise the structure of formula I.

3. The modified oligonucleotide according to embodiment 2, wherein all of the nucleotides of the oligonucleotide are independently modified at the 2' position to comprise the structure of formula I.

4. The modified oligonucleotide according to any one of embodiments 1 to 3, wherein $R^1$, $R^2$, $R^3$ and $R^4$ are independently selected from hydrogen and methyl.

5. The modified oligonucleotide according to any one of embodiments 1 to 4, wherein $R^1$, $R^2$, $R^3$ and $R^4$ represent hydrogen.

6. The modified oligonucleotide according to any one of embodiments 1 to 5, wherein p is 1.

7. The modified oligonucleotide according to any one of embodiments 1 to 6, wherein q is 1.

8. The modified oligonucleotide according to any one of embodiments 1 to 7, wherein said Base is selected from adenine, 2,6-diaminopurine, guanine, cytosine, 5-methylcytosine, uracil and thymine.

9. The modified oligonucleotide according to any one of embodiments 1 to 8, wherein said modified nucleotides are independently modified at the 2' position to comprise a structure selected from:
2'-O-aminoethylcarbamoylmethyladenosine;
2'-O-aminoethylcarbamoylmethylcytidine;
2'-O-aminoethylcarbamoylmethyl-2-aminoadenosine;
2'-O-aminoethylcarbamoylmethylguanosine;
2'-O-aminoethylcarbamoylmethyl-5-methyluridine;
2'-O-aminoethylcarbamoylmethyluridine; and
2'-O-aminoethylcarbamoylmethyl-5-methylcytidine.

10. The modified oligonucleotide according to embodiment 9, wherein said modified nucleotides are independently modified at the 2' position to comprise one or more of the structures selected from:
2'-O-aminoethylcarbamoylmethyladenosine;
2'-O-aminoethylcarbamoylmethylcytidine;
2'-O-aminoethylcarbamoylmethylguanosine; and
2'-O-aminoethylcarbamoylmethyluridine.

11. The modified oligonucleotide according to embodiment 9 or 10, wherein said modified nucleotides are modified at the 2' position to comprise the structure of 2'-O-aminoethylcarbamoylmethyladenosine.

12. The modified oligonucleotide according to any one of embodiments 1 to 11, wherein the oligonucleotide comprises from 9 to 30 nucleotide residues.

13. The modified oligonucleotide according to any one of embodiments 1 to 12, wherein the modified oligonucleotide comprises a further moiety selected from fatty acid and steroid derivatives, peptides, carbohydrates, drugs, reporter molecules, and nuclear localisation signals; and wherein said further moiety is conjugated with a non-modified nucleotide and/or with a modified nucleotide via another nucleotide moiety than with the 2' substituent of the modified structure of formula I.

14. A precursor of a modified nucleotide, which nucleotide is modified at the 2' position to comprise the structure of formula I:

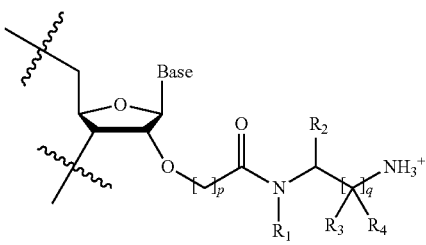

I wherein
Base is a purine or pyrimidine moiety;
R¹ and R² are independently selected from hydrogen and $C_1$-$C_3$ alkyl;
R³ is selected from hydrogen and $C_1$-$C_6$ alkyl;
R⁴ is selected from hydrogen and $C_1$-$C_{16}$ alkyl;
p=1 or 2.
q=1 or 2; and
which precursor is comprising the structure of formula I and one or more protecting groups.

15. A precursor according to embodiment 14 wherein said protecting groups are selected from:
  5'-protecting groups, such as 4-monomethoxytrityl, 4,4'-dimethoxytrityl, pixyl and silyl groups;
  base protecting groups, such as acyl groups (e.g. acetyl, isobutyryl, phenylacetyl, propionyl, etc) or amidine protecting group (e.g. (dimethylamino)ethylidene, N-methylpyrrolidin-2-ylidene, etc.);
  phosphate and thiophosphate protecting groups, such as cyanoethyl, methyl, acylated aminoethyl and aminopropyl groups; and
  amino protecting groups, such as trifluoroacetyl, carbamates and acyl groups, removable under conditions where oligonucleotides are not degraded, e.g. fluorenylmethyloxycarbonyl (Fmoc) etc.

16. A precursor according to embodiment 14 or 15, selected from:
N⁶-Benzoyl-5'-O-(4-monomethoxytrityl)-2'-O-(2-N-trifluoroacetamido-ethyl)carbamoylmethyl)adenosine 3'-O-[Cyanoethyl(N,N-diisopropylamino)-phosphoramidite;
N⁴-Acetyl-5'-O-(4-monomethoxytrityl)-2'-O—[(N-(trifluoroacetamido-ethyl)carbamoyl)methyl]cytidine;
N²,N⁶-Diacetyl-5'-O-(4-monomethoxytrityl)-2'-O—(N-(trifluoroacetamido-ethyl)carbamoyl)methyl-2,6-diaminopurin-9-yl riboside;
5'-O-(4-Monomethoxytrityl)-N²-(Phenoxyacetyl)-2'-O—(N-(trifluoro-acetamidoethyl)carbamoyl)methylguanosine;
5'-O-(4-Monomethoxytrityl)-2'-O—[(N-(trifluoroacetamidoethyl)-carbamoyl)methyl]uridine;
5'-O-(4-Monomethoxytrityl)-2'-O—(N-(trifluoroacetamidoethyl)-carbamoyl)methyl-N⁶-butyryladenosine 3'-H-phosphonate triethylammonium salt;
3'-O—(N,N-Diisopropylamino-(2-cyanoethoxy)phosphinyl)-5'-O-(4-methoxytrityl)-2'-O—[(N-(trifluoroacetamidoethyl)carbamoyl)-methyl]uridine;
3'-O—(N,N-Diisopropylamino-(2-cyanoethoxy)phosphinyl)-5'-O-(4-methoxytrityl)-N²-(phenoxyacetyl)-2'-O—[(N-(trifluoroacetamidoethyl)-carbamoyl)methyl]guanosine; and
N⁴-Acetyl-3'-O—(N,N-diisopropylamino-(2-cyanoethoxy) phosphinyl)-5'-O-(4-methoxytrityl)-2'-O—[(N-(trifluoroacetamidoethyl)carbamoyl)-methyl]cytidine.

17. Use of one or more modified nucleotides, which are independently modified at the 2' position to comprise the structure of formula I, and optionally further comprising one or more protecting groups:

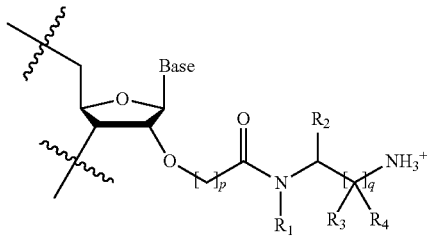

I wherein
Base is a purine or pyrimidine moiety;
R¹ and R² are independently selected from hydrogen and $C_1$-$C_3$ alkyl;
R³ is selected from hydrogen and $C_1$-$C_6$ alkyl;
R⁴ is selected from hydrogen and $C_1$-$C_{16}$ alkyl;
p=1 or 2; and
q=1 or 2,
in a modified oligonucleotide of 5-50 nucleotide residues according to any one of embodiments 1 to 12 to enhance the capacity of uptake into human cells of the modified oligonucleotide.

18. A pharmaceutical composition comprising a modified oligonucleotide according to any one of embodiments 1 to 13, together with a pharmaceutically acceptable carrier and/or excipient.

19. The modified oligonucleotide or composition according to any one of embodiments 1 to 13 or 18 for use as a medicament.

20. A method for manufacturing a modified oligonucleotide of 5-50 nucleotide residues according to any one of embodiments 1 to 13 with enhanced capacity of uptake into human cells, comprising the step of incorporating one or more modified nucleotides into said modified oligonucleotide, which modified nucleotides are independently modified at the 2' position to comprise the structure of formula I, and optionally further comprising one or more protecting groups:

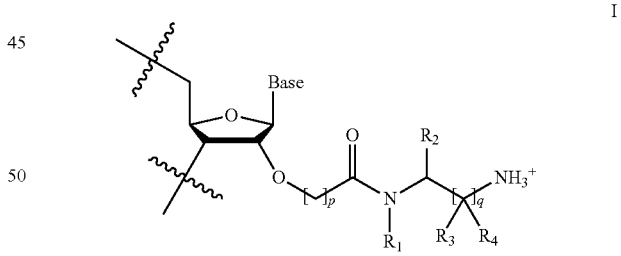

I wherein
Base is a purine or pyrimidine moiety;
R¹ and R² are independently selected from hydrogen and $C_1$-$C_3$ alkyl;
R³ is selected from hydrogen and $C_1$-$C_6$ alkyl;
R⁴ is selected from hydrogen and $C_1$-$C_{16}$ alkyl;
p=1 or 2; and
q=1 or 2.

21. A method for treating, alleviating or preventing a disease, comprising administering to a patient in need thereof, a therapeutically effective amount of a modified oligonucleotide according to any one of embodiments 1 to 13.

DETAILED DESCRIPTION OF THE INVENTION

Oligonucleotides containing a substantial degree of the AECM modification (FIG. 1) and/or structurally related modifications exhibits an increase in melting point of duplexes and enhanced cellular uptake of the oligonucleotide, which makes these modifications surprisingly suitable for enhancement of drug uptake into human cells in oligonucleotide based therapy and possibly also as vectors for other drugs.

In a first aspect, the present invention provides a modified oligonucleotide of 5-50 nucleotide residues, wherein at least 25% of the nucleotides are independently modified at the 2' position to comprise the structure of formula I:

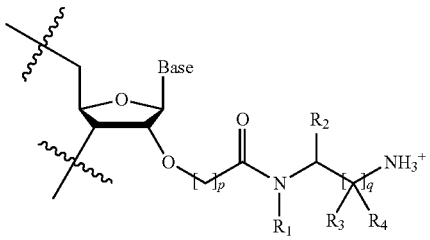

I wherein
Base is a purine or pyrimidine moiety;
$R^1$ and $R^2$ are independently selected from hydrogen and $C_1$-$C_3$ alkyl;
$R^3$ is selected from hydrogen and $C_1$-$C_6$ alkyl;
$R^4$ is selected from hydrogen and $C_1$-$C_{16}$ alkyl;
p=1 or 2; and
q=1 or 2.

Thus, it has now surprisingly been realized that the capacity for cellular uptake of an oligonucleotide is enhanced by replacing the hydrogen or hydroxyl group at the 2' carbon with a 2-O'—(N-aminoalkyl)carbamoyl(m) ethyl structure as set out above in a substantial amount of the nucleotide residues, i.e. at least 25%. This also implies that at least 2 of the nucleotide residues in the modified oligonucleotide are modified as set out above. The term "modified oligonucleotide" encompasses all types of native and synthetic oligonucleotides, including DNA, RNA or DNA/RNA oligonucleotides, which have been modified at least at the 2' position to comprise the structure of formula I.

It is preferred that at least 50%, such as at least 60% or at least 70%, preferably at least 80%, such as at least 90%, or even all of the nucleotides of the oligonucleotide are independently modified at the 2' position to comprise the structure of formula I. It has been realized that the capacity of cellular uptake of the resulting oligonucleotide incorporating the modified nucleotides appears to be governed by degree of modification.

By the term "alkyl" as used herein, is meant both straight, cyclic and branched chain saturated hydrocarbon groups. Examples of alkyl groups include methyl, ethyl, n-propyl, iso-propyl, n-butyl, iso-butyl, sec-butyl, and t-butyl groups. Among unbranched alkyl groups, there are preferred methyl, ethyl, n-propyl, and n-butyl groups. Among branched alkyl groups, there may be mentioned iso-propyl, iso-butyl, sec-butyl, and t-butyl groups.

In the structure of formula I, it is according to one embodiment preferred that $R^3$ and $R^4$ are independently selected from hydrogen and $C_1$-$C_6$ alkyl, and preferably from hydrogen and $C_1$-$C_3$ alkyl. In another preferred embodiment, $R^3$ is selected from hydrogen and $C_1$-$C_3$ alkyl, and $R^4$ is selected from $C_6$-$C_{16}$ alkyl.

In the structure of formula I, it is according to one embodiment preferred that $R^1$, $R^2$, $R^3$ and $R^4$ are independently selected from hydrogen and methyl, and that they preferably all represent hydrogen. It is preferred that p is 1. It is also preferred that q is 1.

In preferred embodiments of the invention, the Base of formula I is selected from adenine, 2,6-diaminopurine, guanine, cytosine, 5-methylcytosine, uracil and thymine. In preferred embodiments of the invention, the modified nucleotides are independently modified at the 2' position to comprise a structure selected from:
2'-O-aminoethylcarbamoylmethyladenosine;
2'-O-aminoethylcarbamoylmethylcytidine;
2'-O-aminoethylcarbamoylmethyl-2-aminoadenosine;
2'-O-aminoethylcarbamoylmethylguanosine;
2'-O-aminoethylcarbamoylmethyl-5-methyluridine;
2'-O-aminoethylcarbamoylmethyluridine; and
2'-O-aminoethylcarbamoylmethyl-5-methylcytidine.

In preferred embodiments of the invention, the modified nucleotides are independently modified at the 2' position to comprise one or more of the structures selected from:
2'-O-aminoethylcarbamoylmethyladenosine;
2'-O-aminoethylcarbamoylmethylcytidine;
2'-O-aminoethylcarbamoylmethylguanosine; and
2'-O-aminoethylcarbamoylmethyluridine.

In a preferred embodiment of the invention, the modified nucleotides are modified at the 2' position to comprise the structure of 2'-O-aminoethylcarbamoylmethyladenosine.

The modified oligonucleotide according to the present invention comprises from 3 to 100 nucleotide residues, and preferably 5-50 nucleotide residues. In preferred embodiments of the invention, the modified oligonucleotide comprises from 9 to 50 nucleotide residues or from 5 to 30 nucleotide residues, such as from 9 to 30 nucleotide residues, or from 16 to 30 nucleotide residues.

The oligonucleotides of the present invention exhibit an increased stability, as compared with oligonucleotides lacking said modified nucleotides. This may be tested by incubating the oligonucleotides with modified nucleotides in human serum, for about 12-24 h and comparing the stability with an oligonucleotide where the respective nucleotides have not been replaced with modified nucleotides, e.g. as set out in Example 10. The resulting amount of remaining, non-degraded oligonucleotide may be measured by HPLC techniques.

In specific embodiments, the modified oligonucleotide according to the invention is comprising a further moiety selected from fatty acid and steroid derivatives, peptides, carbohydrates, drugs, reporter molecules (e.g. fluorescent, radioactive or enzyme-based reporter molecules), and nuclear localisation signals. It shall be noted that any such further moiety is not conjugated with any 2-O'—(N-aminoalkyl)carbamoyl(m)ethyl modification according to the invention, since it has now been realized that this substituent provide the enhanced cellular uptake which is the basis for the present invention. It follows that any such further moiety is conjugated with a non-modified nucleotide and/or with a modified nucleotide, and in that case via another nucleotide moiety than with the 2' substituent of the modified structure of formula I.

In particular, the AECM modification included in a therapeutic oligonucleotide to promote the cellular uptake could be combined with other uptake enhancing or tissue targeting entities by conjugation to the aforementioned oligonucleotide. Embodiments of particular interest include oligonucleotides containing a sufficient number of AECM modifications for enhanced cellular uptake, conjugated to entities such as, but not limited to, fatty acid and steroid deriviatives and peptides that further enhance endosomal escape and hence uptake in to the interior of the cell as well as to organ or tumor homing peptides or carbohydrates that promote targeting of specific tissues. Prodrugs are also included, i.e. chemicals that are converted to a oligonucleotide according to formula I, in vivo on oxidation, reduction or hydrolysis.

According to another aspect, the present invention provides novel intermediates, or precursors, which are useful in the manufacturing of the modified oligonucleotides. There is provided a precursor of a modified nucleotide, which nucleotide is modified at the 2' position to comprise the structure of formula I:

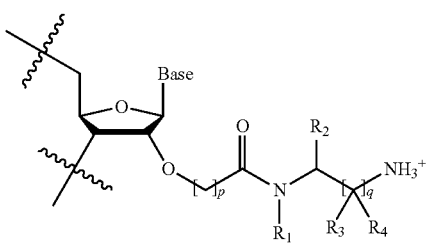

I wherein
Base is a purine or pyrimidine moiety;
$R^1$ and $R^2$ are independently selected from hydrogen and $C_1$-$C_3$ alkyl;
$R^3$ is selected from hydrogen and $C_1$-$C_6$ alkyl;
$R^4$ is selected from hydrogen and $C_1$-$C_{16}$ alkyl;
p=1 or 2.
q=1 or 2; and
which precursor is comprising the structure of formula I and one or more protecting groups.

Suitable protecting groups for these precursors are well known to the skilled person.

Examples of 5'-protecting groups are: 4-monomethoxytrityl, 4,4'-dimethoxytrityl, pixyl and silyl groups.

Examples of base protecting groups (on the purines or pyrimidines) are: acyl groups (e.g. acetyl, isobutyryl, phenylacetyl, propionyl, etc) or amidine protecting group (e.g. (dimethylamino)ethylidene, N-methylpyrrolidin-2-ylidene, etc.).

Examples of phosphate and thiophosphate protecting groups are cyanoethyl, methyl, acylated aminoethyl and aminopropyl groups etc.

The diisopropylamino group could be replaced by other amino groups, such as e.g., dimethylamino, diethylamino, and pyrrolidino groups etc.

Examples of amino protecting groups are: trifluoroacetyl, carbamates and acyl groups, removable under conditions where oligonucleotides are not degraded, e.g. fluorenylmethyloxycarbonyl (Fmoc) etc.

Specifically, there is provided precursors of the modified nucleotides according to the invention, selected from:
$N^6$—Benzoyl-5'-O-(4-monomethoxytrityl)-2'-O-(2-N-trifloroacetamido-ethyl)carbamoylmethyl)adenosine 3'-O-[Cyanoetyl(N,N-diisopropylamino)-phosphoramidite;
$N^4$-Acetyl-5'-O-(4-monomethoxytrityl)-2'-O—[(N-(trifluoroacetamido-ethyl)carbamoyl)methyl]cytidine;

$N^2,N^6$-Diacetyl-5'-O-(4-monomethoxytrityl)-2'-O—(N-(trifluoroacetamido-ethyl)carbamoyl)methyl-2,6-diaminopurin-9-yl riboside;
5'-O-(4-Monomethoxytrityl)-$N^2$-(Phenoxyacetyl)-2'-O—(N-(trifluoro-acetamidoethyl)carbamoyl)methylguanosine;
5'-O-(4-Monomethoxytrityl)-2'-O—[(N-(trifluoroacetamidoethyl)-carbamoyl)methyl]uridine;
5'-O-(4-Monomethoxytrityl)-2'-O—(N-(trifluoroacetamidoethyl)-carbamoyl)methyl-$N^6$-butyryladenosine 3'-H-phosphonate triethylammonium salt;
3'-O—(N,N-Diisopropylamino-(2-cyanoethoxy)phosphinyl)-5'-O-(4-methoxytrityl)-2'-O—[(N-(trifluoroacetamidoethyl)carbamoyl)-methyl]uridine;
3'-O—(N,N-Diisopropylamino-(2-cyanoethoxy)phosphinyl)-5'-O-(4-methoxytrityl)-$N^2$-(phenoxyacetyl)-2'-O—[(N-(trifluoroacetamidoethyl)-carbamoyl)methyl]guanosine; and
$N^4$-Acetyl-3'-O—(N,N-diisopropylamino-(2-cyanoethoxy)phosphinyl)-5'-O-(4-methoxytrityl)-2'-O—[(N-(trifluoroacetamidoethyl)carbamoyl)-methyl]cytidine.

Optionally, the 4-monomethoxytrityl could be replaced by other 5'-protecting groups, such as 4,4'-dimethoxytrityl, pixyl and silyl groups.

Optionally, the acyl groups on the purines or pyrimidines could be replaced by other known base protecting groups, such as another acyl group (e.g. isobutyryl, phenylacetyl, propionyl, etc) or amidine protecting group (e.g., (dimethylamino)ethylidene, N-methylpyrrolidin-2-ylidene, etc.).

Optionally, the cyanoethyl group on a phosphoroamidite could be replaced with other phosphate and thiophosphate protecting groups, such as e.g., methyl, acylated aminoethyl and aminopropyl groups etc.

Optionally, the diisopropylamino group could be replaced by other amino groups, such as e.g., dimethylamino, diethylamino, and pyrrolidino groups etc.

Optionally, the trifluoroacetyl group could be replaced by other amino protecting groups, such as carbamates and acyl groups, removable under conditions where oligonucleotides are not degraded, e.g. fluorenylmethyloxycarbonyl (Fmoc) etc.

According to a further aspect, the present provides a novel use of one or more modified nucleotides, which are independently modified at the 2' position to comprise the structure of formula I, and optionally further comprising one or more protecting groups:

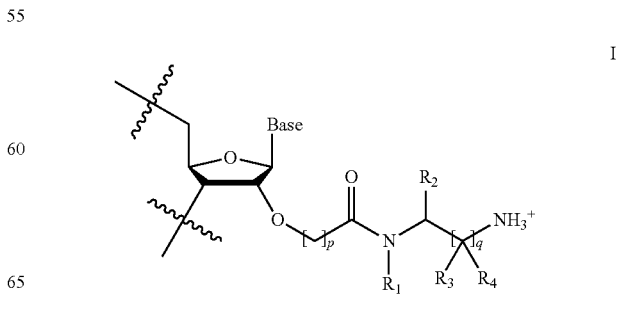

I wherein
  Base is a purine or pyrimidine moiety;
  $R^1$ and $R^2$ are independently selected from hydrogen and $C_1$-$C_3$ alkyl;
  $R^3$ is selected from hydrogen and $C_1$-$C_6$ alkyl;
  $R^4$ is selected from hydrogen and $C_1$-$C_{16}$ alkyl;
  p=1 or 2; and
  q=1 or 2,
in a modified oligonucleotide of 5-50 nucleotide residues according to the invention to enhance the capacity of uptake into human cells of the modified oligonucleotide. Put another way, the present invention also provides the use of one or more modified nucleotides and/or precursors thereof as set out above, optionally further comprising protecting groups, in the manufacture of a modified oligonucleotide of 5-50 nucleotide residues according to the invention to enhance the capacity of uptake into human cells of the modified oligonucleotide. It is preferable that the novel precursors according to the present invention are used for incorporating one or more modified nucleotides into said modified oligonucleotide.

According to a related aspect, the present invention provides a method for manufacturing a modified oligonucleotide of 5-50 nucleotide residues according to the invention with enhanced capacity of uptake into human cells. The method comprises the step of incorporating one or more modified nucleotides into said modified oligonucleotide, which modified nucleotides are independently modified at the 2' position to comprise the structure of formula I, and optionally further comprising one or more protecting groups:

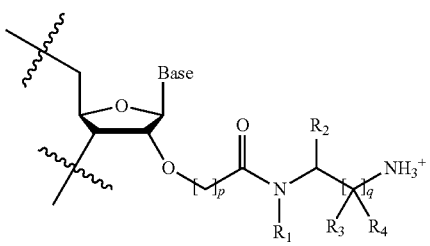

I wherein
  Base is a purine or pyrimidine moiety;
  $R^1$ and $R^2$ are independently selected from hydrogen and $C_1$-$C_3$ alkyl;
  $R^3$ is selected from hydrogen and $C_1$-$C_6$ alkyl;
  $R^4$ is selected from hydrogen and $C_1$-$C_{16}$ alkyl;
  p=1 or 2; and
  q=1 or 2.

It is preferable that the novel precursors according to the present invention are used in the step of incorporating one or more modified nucleotides into said modified oligonucleotide.

These uses and manufacturing methods occur in vitro, prior to administration of the resulting modified oligonucleotide to a human patient in need thereof.

By the term "cellular uptake" as used herein, is meant the ability to taken up into the interior of cells, in endosomal vesicles or into the cytoplasm. The oligonucleotides containing a substantial amount of the structure of the present invention exhibit an effect by which the cellular uptake is increased. An enhanced capacity for cellular uptake may be measured by comparison of said uptake with an oligonucleotide where the respective nucleotides have not been replaced with modified nucleotides, e.g. as set out in Example 11.

According to another aspect, the present invention provides a pharmaceutical composition comprising a modified oligonucleotide according to the invention, together with a pharmaceutically acceptable carrier and/or excipient. According to a related aspect, the present invention provides the modified oligonucleotide or composition according to the invention for use as a medicament. According to a further related aspect, the present invention provides a method for treating, alleviating or preventing a disease, comprising administering to a patient in need thereof, a therapeutically effective amount of a modified oligonucleotide according to the invention.

In a further aspect, the invention provides a design for enhancing uptake of oligonucleotide-containing drugs for treating, preventing or counteracting disease, by administering a medicament comprising of an effective amount of at least one compound containing a sufficient number of units of formula I as defined above, in order to enhance the uptake and hence efficiency of the drug.

Said oligonucleotide may be administered by intraperitoneal or intravenous injection or in an oral dosage form, such as but not limited to a tablet, a capsule, a solution, a suspension, a powder, a paste, an elixir, and a syrup. Other administration forms are also useful, these include but not are limited to topical administration forms, which are in particular useful against certain skin diseases or infections of the skin, these include for example creams, oils, lotions, and ointments. Yet further dosage forms include dosage forms for delivery to the respiratory system including the lungs, such as aerosols and nasal spray devices or transmucosal or injectable formulations Oligonucleotide therapy has a rather short history, but a great potential for several reasons. Since a decade the whole human genome sequence is known in detail, i.e. the potential target sequences are already available. Initially, single-stranded DNA fragments to inhibit mRNA of target genes, so-called antisense ONs, were used but today the field encompasses therapeutic ONs with a number of different modes of action. Collectively, this tremendous progress demonstrates that the field of therapeutic ONs holds great promise for future drugs. In parallel the costs for synthesizing ONs have been increasingly reduced. The beauty with genetic drugs is that their design is much more straightforward and predictable as compared to small molecule drugs. Moreover, there are many proteins considered to be essentially "undruggable", owing to that their surfaces lack suitable regions to which small molecules can bind (e.g. many transcription factors belong to this group). However, since genetic drugs target RNA or DNA, protein 3-D structure is no limitation. The bottleneck is instead their delivery, since these molecules are generally too large to readily be taken up by cells.

An approach where the oligonucleotide therapeutic by itself has cell-penetrating properties, as well as additional functional entities, gives the possibility to create oligonucleotide based nano-structures that efficiently enters cells where the target for the oligonucleotide therapy resides, thereby making the therapy considerably more effective.

The synthesis of 2'-O—(N-(aminoethyl)carbamoyl) methyl (AECM) modified building blocks is exemplified in Schemes 1 to 6. For example, 5'-O-(4-monomethoxytrityl) adenosine (1) was treated with potassium tertbutoxide in THF and then reacted with allyl bromoacetate. Subsequent treatment was performed with ethylenediamine and then trifluoroacetic acid anhydride TFAA after evaporation of excess EDA. After work-up and chromatography the modified AECM-nucleoside 2 was obtained.

Compound 2 was then base protected by benzoylation to give 3. This material was further treated with 2-cyanoethyl diisopropylchlorophosporamidite following standard procedures for phosphoramidite synthesis. After chromatography, phosphoroamidite 4 ready for oligonucleotide synthesis was obtained (as the R,S-phosphoramidite mixture, Scheme 1).

The phosphoramidite 4 was further used in oligonucleotide synthesis to obtain several oligonucleotides containing the 2'-O-AECM modification (SEQ ID NOs 1, 3, 5, 7 and 9).

Thermal melting of duplexes between the 2'-O-AECM containing oligonucleotides with SEQ ID NOs 1, 3, 5, and 7 and complementary RNA and DNA sequences was then performed. The thermal melting of the duplexes were also compared to those obtained between the corresponding non-modified ("native") oligodeoxynucleotides SEQ ID NOs 2, 4, 6, and 8 and the same complementary sequences. The results showed that in the duplexes with DNA, the modification was tolerated or gave a slight increase in the melting. With the duplexes with complementary RNA, some sequence dependence was observed. However, a clear and substantial stabilisation was obtained with both fully and partially AECM modified oligonucleotides, as evidenced by higher thermal melting points (up to +2.3 degrees per modification).

To investigate the stability of oligonucleotides in biological fluids, the substantially 2'-O-AECM modified oligonucleotide with SEQ ID NO 7 was subjected to incubation in human serum (90%). A non-modified DNA (SEQ ID NO 8) with the same base sequence was also subjected to the same conditions as a comparison. The HPLC analysis after 24 h displays that the non-modified DNA is completely degraded, but the 2'-O-AECM modified oligonucleotide is still intact. Thus, the AECM modification renders the oligonucleotide stable towards enzymatic degradation in human serum.

To evaluate cellular uptake of AECM-modified oligonucleotides, two oligonucleotides (one fully AECM-modified and one non-modified; SEQ ID NOs 9 and 10, respectively) and both carrying a fluorescent label (a fluorescein derivative) were synthesized. Human U20S cells were then treated with the respective oligonucleotides, washed, and fluorescence and confocal microscopy was used to visualize if the oligonucleotides had been taken up by the cells. The results clearly show that the non-modified oligonucleotides are not taken up while there is substantial cellular uptake of the AECM-modified oligonucleotides.

Inclusion of the 2'-O-AECM and related structural modifications in oligonucleotides provides remarkable properties to the oligonucleotide, such as a substantially increased cellular uptake of the modified oligonucleotide, in addition to enhancing binding to a target nucleic acid and increased resistance to degradation in human serum. These findings are all most valuable properties for an oligonucleotide drug. In particular the cell penetrating properties of AECM containing oligonucleotides should make these most useful in oligonucleotide therapy where cellular uptake is quite limiting for the efficiency.

The prevailing notion for modified oligonucleotides is that there is generally a trade-off between efficiency of cellular uptake on the one hand, and nuclease resistance on the other (Gary D. Gray, et al. *Biochemical Pharmacology*, 1997, 53, 1465-1476). The findings according to the present invention, i.e. that an efficient cellular uptake can be obtained in combination with a favourable nuclease stability, are therefore very surprising.

As mentioned, an important aspect of the invention provides methods for treating, preventing or counteracting diseases with an effective amount of at least one oligonucleotide according to the invention, where efficacy is increased by increased uptake and also where a lower dose gives as good efficacy while allowing a lower toxicity. Useful embodiments that benefit from treatment according to the invention are in particular those relating to RNA splice-correcting or splice-switching therapy, since these approaches are not dependent on recognition by cellular RNase H. The modified oligonucleotides according to the invention are also applicable to other genetic diseases. Such conditions and diseases include but are not limited to Duchenne Muscular Dystrophy, Huntingdons disease, viral diseases and cancers.

Preferably, the medicament is administered orally, but other administration routes are within the scope of the invention and may be more suitable for certain conditions. Such other administration routes include topical, buccal nasal, parenteral, including rectal and vaginal administration. It is contemplated that, in addition to the resistance to degradation, it is the increased cellular uptake resulting from incorporation of the modified nucleotides that allows for oral administration.

Examples of suitable formulations for topical use include creams, ointments, gels, or aqueous or oily solutions or suspensions. Parenteral administration can be accomplished for example by formulating the compound as a sterile aqueous or oily solution for intravenous, subcutaneous, or intramuscular dosing or as a suppository for rectal dosing.

Another aspect of the invention relates to a pharmaceutical composition for treating, preventing or counteracting any of the above mentioned conditions or diseases. The compositions comprise at least one of the compounds described herein together with at least one pharmaceutically acceptable excipient.

The compositions can be formulated in various suitable forms, depending on which conditions they are primarily aimed at. In certain embodiments, the compositions are for oral administration. Such compositions include but are not limited to tablets, capsules, a solution, a suspension, a powder, a paste, an elixir, or a syrup.

The oral composition of the invention may be formulated for delayed and/or extended release and may be enteric coated by means well known to the skilled person, to be released in the lower intestinal tracts.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

The suitable amount of the compound to be administered can vary depending on the selected specific compound(s), the specific location of the infection and condition(s) to be treated and/or prevented. In some embodiments, the amount to be administered can be in the range of about 10 μg to about 25 g. A suitable dosage form can be selected and formulated accordingly. For example, for treatment of diseases and conditions in the gastro-intestinal system a dose in the range of 250 μg to about 25 g may be suitable, including the range of about 1 g to about 25 g, e.g. in the range of about 1 g to 10 g, such as about 1 g, 2 g, 5 g or 10 g.

It will also be appreciated, in particular when it is desired to administer a large amount of active compound, such as, in the range of 1-25 g, (should not this be the same as above), that the compounds of the invention can be formulated and comprised in functional food or feed products. As discussed above, the methods and compositions of the present invention have application in the treatment of both humans as well as other animals, including veterinary and animal husbandry applications for companion animals, farm animals, and ranch animals. These applications include but are not limited to treating, preventing or counteracting diseases and conditions in dogs, cats, cows, horses, deer and poultry including hen, turkey ducks, geese; as well as in household pets such as birds and rodents. For large animals, a suitable dose can be larger than the above mentioned amounts.

The invention will be illustrated by the following non-limiting examples.

EXAMPLES

Example 1

Modified Adenosine Derivatives

Synthesis of the AECM-adenosine derivative $N^6$-Benzoyl-5'-O-(4-monomethoxytrityl)-2'-O-(2-N-trifloroacetamidoethyl)carbamoylmethyl)-adenosine 3'-O-Cyanoetyl(N,N-diisopropylamino)phosphoramidite (4) being a precursor for 2'-O-aminoethyl-carbamoylmethyladenosine in oligonucleotides of the invention

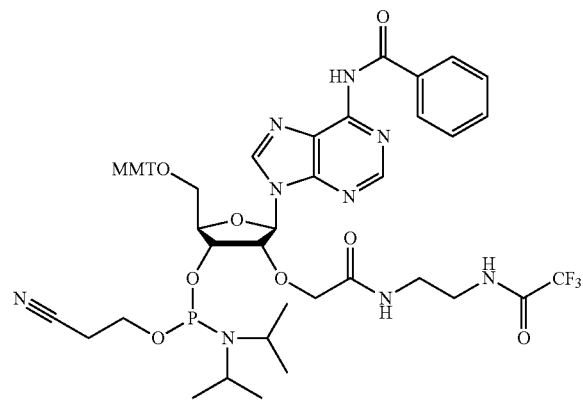

4

Synthesis of 5'-O-monomethoxytrityl-2'-O—(N-(trifluoroacetamidoethyl)-carbamoyl)methyladenosine (2)

Compound 1 (2.50 g, 4.77 mmol) was dried by evaporation of added dry tetrahydrofuran (THF, distilled from LiAlH$_4$ LAH)) and then dissolved in 200 ml dry THF. Potassium tertbutoxide (0.696 g, 6.20 mmol) was added and after 15 min allyl bromoacetate (1.12 g, 6.20 mmol). The reaction was stirred for 2 h and TLC showed that all of compound 1 was consumed. The THF was evaporated under reduced pressure and 100 ml EtOH (99.8% dried over 3 Å molecular sieves) and ethylenediamine (2.87 g, 47.7 mmol) was added. The reaction mixture was stirred for 2 h and 100 ml dry THF was added and the reaction was left over night at room temperature. TLC showed complete conversion of the alkylated products. The solvent was evaporated and the excess ethylenediamine was removed by co-evaporation with added dioxane four times (4×15 ml). The solid material was dissolved in 200 ml dry CH$_2$Cl$_2$ and triethylamine (1.45 g, 14.31 mmol) and trifluoroacetic anhydride (TFAA, 1.65 g, 7.85 mmol) were added. TLC showed that the reaction was complete after 2 h at RT. The reaction mixture was washed with a total of 400 ml water/brine 1:1. The organic layer was dried with MgSO$_4$ and concentrated. The crude product was purified by column chromatography on silica using CH$_2$Cl$_2$/methanol (15:1 with 0.005% triethylamine) as eluent giving 2.7 g (77%) of 2 as a white foam. A slightly modified version of this reaction was performed with methyl bromoacetate instead of the allyl reagent, with the difference that the ethylenediamine was dried first by two times evaporation of added n-butanol and then three times with dioxane. The same product 2 was then obtained in a total yield of 72%. Elemental analysis: Calcd. For $C_{36}H_{36}N_7O_7F_3$: C, 58.77; H, 4.93; N, 13.33. Found: C, 58.57; H, 5.03; N, 13.16.

$^1$H NMR (400 MHz, DMSO-d$_6$): δ=3.14-3.30 (m, 6H, CH$_2$-ethylene, 5'-Ha, 5'-Hb), 3.72 (s, 3H, CH$_3$-trityl), 4.02-4.18 (m, 3H, CH$_2$-carbamoyl, 4'-H), 4.50-4.63 (m, 2H, 2'-H, 3'-H), 5.48 (d, J=6.4 Hz, 1H, 3'-OH), 6.13 (d, J=3.1 Hz, 1H, 1'-H), 6.80 (d, J=9.2 Hz, 2H, trityl), 7.15-7.38 (m, 12H, trityl), 8.12 (s, 1H, H2-base), 8.25 (s, 1H, H8-base), 9.48 (br. s, 1H, NH) ppm. $^{13}$C NMR (100.6 MHz, DMSO-d$_6$): δ=37.2, 39.0, 55.1, 63.5, 69.4, 69.5, 81.8, 82.5, 86.0, 86.3, 113.3, 116.1 (q, J=285 Hz), 118.3, 127.0, 127.9, 128.0, 130.1, 135.3, 144.5, 149.2, 153.0, 156.5, 156.8 (q, J=39 Hz), 158.4, 169.5 ppm.

Synthesis of $N^6$-benzoyl-5'-O-(4-monomethoxytrityl)-2'-O-(2-N-trifloroacetamidoethyl)carbamoylmethyl)adenosine 3'-O-Cyanoetyl(N,N-diisopropylamino)phosphoramidite (4)

Compound 2 (2.6 g, 3.53 mmol) was dried twice by evaporation of added acetonitrile (dried over 3 Å molecular sives) and dissolved in 80 ml dry CH$_2$Cl$_2$. To the solution triethylamine (3.94 ml, 28.27 mmol) was added followed by trimethylsilyl chloride (TMS-Cl, 0.902 ml, 7.06 mmol). The reaction was left for 2 h and an additional portion of TMS-Cl (1.77 mmol) was added whereupon the reaction was left for 30 min. A catalytic amount of DMAP (20 mg) was added to the solution. The solution was chilled to −10° C. and benzoyl chloride (0.819 ml, 7.06 mmol) was added. The reaction was left to reach room temperature and after 3 h another portion of benzoyl chloride (1.77 mmol) was added and the reaction was thereafter left overnight. The solution was extracted with CH$_2$Cl$_2$ (200 ml) and washed twice with a mixture of (H$_2$O 50 ml/brine 50 ml/NaHCO$_3$, 0.1 M, 50 ml) then (H$_2$O 100 ml/brine 100 ml). The organic layer was dried over Na₂SO₄ and evaporated to give a pink foam. The crude product was dissolved in ethanol (60 ml, 99.5%) and ammonium hydroxide (12 ml, 30%) and left for 1 h. Removal of solvent under reduced pressure yielded the crude product which was chromatographed on silica gel using CH₂Cl₂-MeOH (10:1 containing 0.05% triethylamine) as eluent yielding 3 as a white foam (MS (ES-TOF) [M-H]⁺ calcd for $C_{43}H_{39}F_3N_7O_8$ 838.29. found 838.29). 1.60 g, (1.90 mmol) of 3 was then dried twice by evaporation of added THF (distilled over LAH) and dissolved in dry THF (40 ml). Triethylamine (1.30 ml, 7.60 mmol) was added and then 2-Cyanoethyl N,N-diisopropylchlorophosphoramidite (0.848 ml, 3.8 mmol) was added dropwise with a syringe under nitrogen atmosphere during 2 min. The reaction mixture was left stirring for 30 min and then concentrated until 5 ml of solution remained. To the solution ethyl acetate (150 ml) was added. The crude solution was extracted twice with a mixture of (brine 50 ml/NaCO₃, 10% (aq), 50 ml/H₂O 50 ml). The organic layer was dried over Na₂SO₄ and removal of solvent under reduced pressure yielded the crude product as colorless foam. The crude product was dissolved in ethyl acetate (EtOAc, 10 ml) and was dropped with a syringe into hexane (180 ml) at −78° C. After filtration the precipitate was collected and dried to give a white solid. The solid was chromatographed over silica gel using (EtOAc/MeCN 13:1 containing 1% triethylamine) as eluent yielding 4 (as a mixture of the two phosphorus isomers in a 41 to 59 ratio) (1.86 g, 94%) as white foam. ¹H-NMR (CDCl₃): 1.05-1.25 (m, 12H, CH₃-iPr); 2.30-2.65 (m, 2H, CH-iPr); 3.30-3.70 (m, 6H, 5H'+2*CH₂-ethylenediamine); 3.50-2.75 (m, 4H, CH₂-ethylene-CN); 3.75 (s, 3H, CH₃-trityl); 4.05-4.30 (m, 2H, CH₂-carbamoyl); 4.40-4.45 (m, 1H, 4H'); 4.55-4.65 (m, 1H, 3H'); 4.75 (m, 1H, 2H'); 6.25 (d, 1H, H1'); 6.80 (d, 2H, trityl); 7.25-7.60 (m, 17H, trityl+benzoyl); 8.25 (s, 1H, H2-base); 8.80 (s, 1H, H8-base). ³¹P NMR (CDCl₃): 151 ppm (relative to external 85% H₃PO₄). MS (ES-TOF) [M-H]⁺ calcd for $C_{52}H_{57}F_3N_9O_8P$=1039.40. found 1039.43.

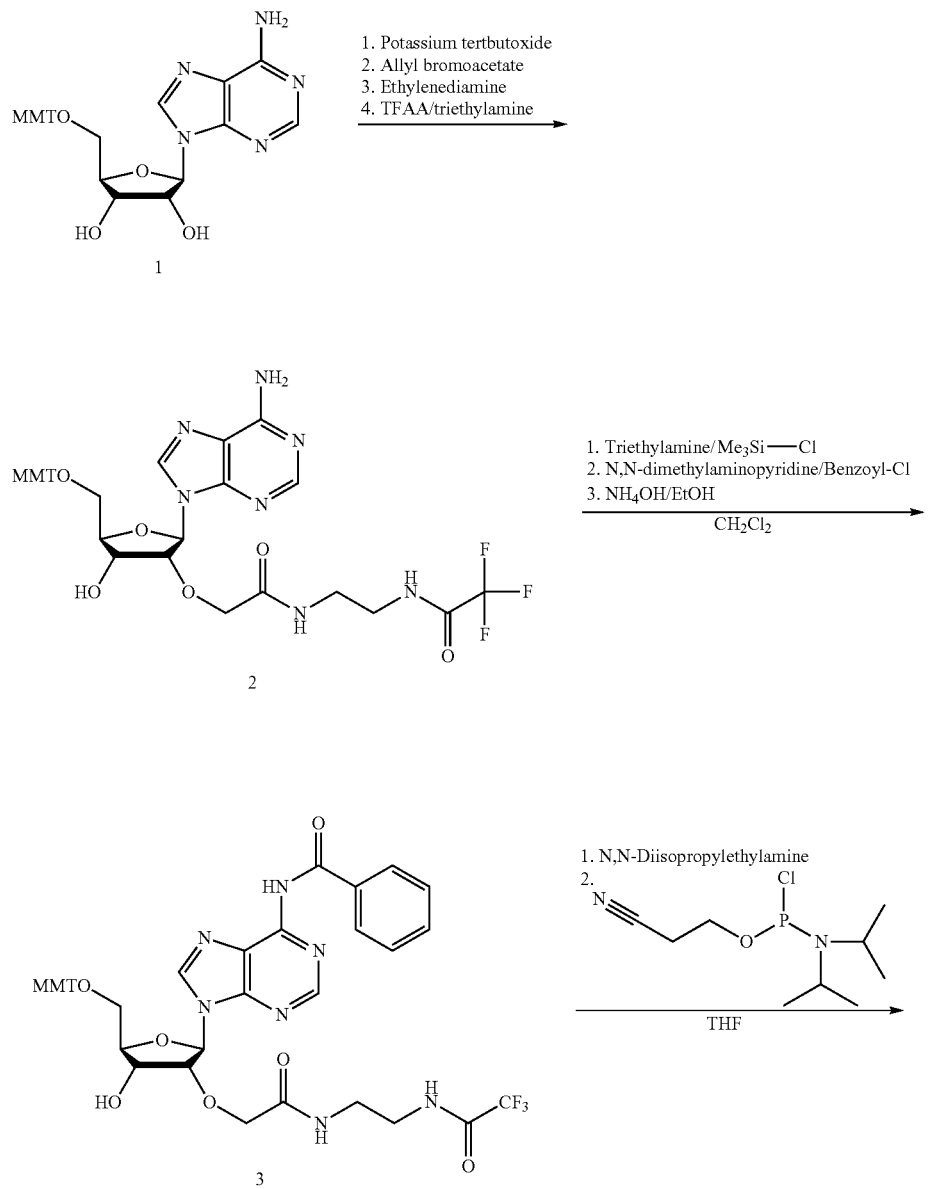

Scheme 1. Synthesis of the AECM-adenosine derivative 4.

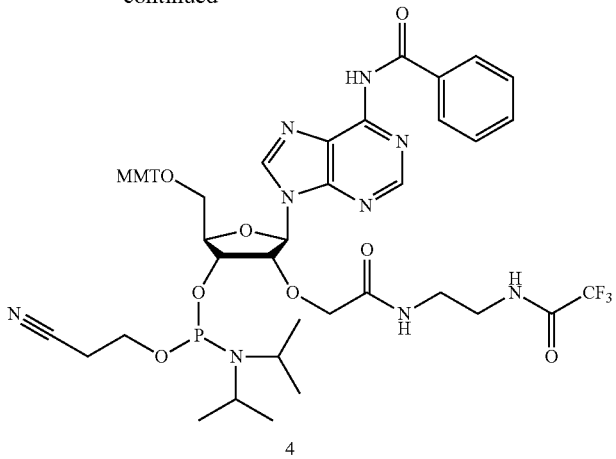

4

Example 2

Modified Cytidine Derivatives

Synthesis of the AECM-cytidine derivative N⁴-Acetyl-5'-O-(4-monomethoxytrityl)-2'-O—[(N-(trifluoro-acetamidoethyl)carbamoyl)-methyl]cytidine (11) being a precursor for 2'-O-aminoethylcarbamoylmethylcytidine in oligonucleotides of the invention

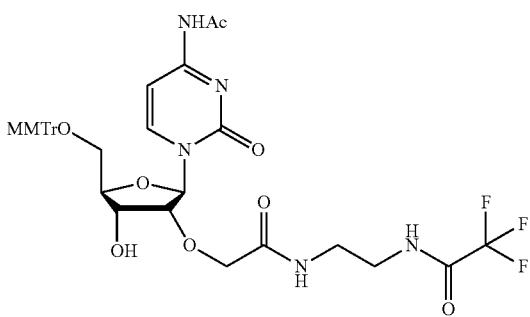

11

3',5'-O-(1,1,3,3-Tetraisopropyl-1,3-disiloxanediyl) cytidine (5)

A suspension of cytidine (1.22 g, 5 mmol) in pyridine (50 mL) was cooled in an ice-water bath and 1,1,3,3-tetraisopropyl-1,3-disiloxanediyl chloride (1.92 mL, 6 mmol) was added dropwise under a nitrogen atmosphere. The reaction mixture was allowed to warm to ambient temperature and stirred for 18 h. The crude reaction mixture was poured onto ice-water and extracted with ethyl acetate (2 times). The organic phase was dried over $Na_2SO_4$, filtered and concentrated under reduced pressure. The residue was subjected to column chromatography using 0 to 10% $CH_3OH$ in $CH_2Cl_2$ as eluent to give compound 5 (2.17 g, 4.47 mmol, 89%). $R_f$=0.55 ($CH_2Cl_2$/$CH_3OH$ 9:1 v/v). Modified from Zhong, M and Strobel, S. A. *J. Org. Chem.* 2008, 73, 603-611.

Modification to the procedure: After completion of the reaction the mixture was poured onto ice-water and extracted with DCM. The organic phase was dried over $Na_2SO_4$, filtered and evaporated.

2'-O—(O-Methylcarboxymethyl)-3',5'-O-(1,1,3,3-tetraisopropyl-1,3-disiloxanediyl)cytidine (6)

Compound 5 (0.5 g, 1.03 mmol) was dissolved in anhydrous DMF (10 mL). The solution was chilled in an ice-water bath, and NaH (60% dispersion in mineral oil, 0.045 g, 1.13 mmol) was added under nitrogen atmosphere. The reaction mixture was stirred for 30 min, methyl 2-bromoacetate (0.107 mL, 1.13 mmol) was added dropwise, and the reaction mixture was stirred for 3 h (TLC ($CH_2Cl_2$/$CH_3OH$ 9:1 v/v). Another portion of NaH (60% dispersion in mineral oil, 0.008 g, 0.2 mmol) and methyl 2-bromoacetate (0.019 mL, 0.2 mmol) were added to the reaction mixture. After the mixture was stirred for an additional hour, glacial acetic acid (0.1 mL) was added, the reaction mixture was stirred for 10 min, and the solvent was evaporated in vacuo. The mixture was dissolved in ethyl acetate and the organic phase was washed with water (2 times), dried over $Na_2SO_4$, filtered and volatiles were evaporated. The residue was subjected to column chromatography using 0 to 6% $CH_3OH$ in $CH_2Cl_2$ as eluent to give compound 6 (0.32 g, 0.57 mmol, 56%). $R_f$=0.63 ($CH_2Cl_2$/$CH_3OH$ 9:1 v/v) and recovered starting material 5 (0.082 g).

2'-O—(N-(Trifluoroacetamidoethyl)carbamoyl) methyl-3',5'-O-(1,1,3,3-tetraisopropyl-1,3-disiloxanediyl)cytidine (8)

Compound 6 (0.3 g, 0.54 mmol) was dissolved in anhydrous methanol (5 mL) and ethylenediamine (0.18 mL, 2.69 mmol) was added at room temperature and the reaction mixture was stirred for 19 h. Volatiles were evaporated in vacuo and the residue was dried by evaporation of added toluene and $CH_2Cl_2$ to give 7. The product was dried in vacuo for 12 h. The crude product (0.295 g, 0.5 mmol) was dissolved in anhydrous methanol (5 mL) and ethyl trifluoroacetate (0.3 mL, 2.51 mmol) was added and the reaction mixture was stirred at room temperature for 20 h. Volatiles were evaporated in vacuo and the residue was purified via flash chromatography using 0 to 10% $CH_3OH$ in $CH_2Cl_2$ as eluent to afford compound 8 (0.235 g, 0.34 mmol, 68% after two steps). $R_f$=0.55 (CH$_2$Cl$_2$/CH$_3$OH 9:1 v/v).

N$^4$-Acetyl-2'-O—[(N-(trifluoroacetamidoethyl)carbamoyl)methyl]cytidine (10)

Acetic anhydride (0.145 mL, 1.54 mmol) was added to a solution of 8 (0.21 g, 0.31 mmol) in anhydrous pyridine (4 mL) and the reaction mixture was stirred at room temperature for 36 h. The reaction was quenched by 10% aqueous NaHCO$_3$ and extracted with CH$_2$Cl$_2$ (3 times). The organic phase was dried over Na$_2$SO$_4$, filtered and concentrated under reduced pressure to afford 9. The crude product (0.195 g, 0.27 mmol) was dissolved in anhydrous tetrahydrofuran-acetonitrile (6 mL, 1:1) and triethylamine trihydrofluoride (0.105 mL, 0.65 mmol) was added and the reaction mixture was stirred at room temperature for 4 h. Volatiles were evaporated in vacuo and the residue was dried by evaporation of added toluene and CH$_2$Cl$_2$. The crude product was purified via flash chromatography using 0 to 15% CH$_3$OH in CH$_2$Cl$_2$ as eluent to afford compound 10 (0.122 g, 0.25 mmol, 95% after two steps). $R_f$=0.21 (CH$_2$Cl$_2$/CH$_3$OH 9:1 v/v).

N$^4$-Acetyl-5'-O-(4-monomethoxytrityl)-2'-O—[(N-(trifluoroacetamidoethyl)carbamoyl)methyl]-cytidine (11)

Compound 10 (0.031 g, 0.064 mmol) was dried by evaporation of added anhydrous pyridine (2 times) and dissolved in 1.2 mL of an anhydrous DMF-DMSO-pyridine (2:1:1) mixture. To the resulted solution triethylamine (0.013 mL, 0.096 mmol) was added followed by the addition of 4-methoxytritylchloride (0.039 g, 0.128 mmol), and the reaction mixture was stirred at ambient temperature for 28 h. The reaction was quenched with 10% aqueous NaHCO$_3$ and the mixture was extracted with ethyl acetate. The organic phase was washed with water (3 times), dried over Na$_2$SO$_4$, filtered and concentrated under reduced pressure. The residue was subjected to column chromatography using 0 to 8% CH$_3$OH in CH$_2$Cl$_2$ as eluent to give compound 11 (0.04 g, 0.053 mmol, 83%). $R_f$=0.48 (CH$_2$Cl$_2$/CH$_3$OH 9:1 v/v). $^1$H NMR (400 MHz, CDCl$_3$): δ=9.03 (br. s, 1H), 8.52 (br. s, 1H), 8.48 (d, J=7.5 Hz, 1H), 8.15 (br. s, 1H), 7.45-7.40 (m, 4H), 7.35-7.20 (m, 9H), 6.86 (d, J=8.8 Hz, 2H), 5.85 (s, 1H), 5.05 (br. s, 1H), 4.53-4.38 (m, 3H), 4.24-4.18 (m, 1H), 3.94 (d, J=4.8 Hz, 1H), 3.80 (s, 3H), 3.64-3.48 (m, 6H), 2.17 (s, 3H) ppm.

Scheme 2. Synthesis of the AECM-cytidine derivative 11.

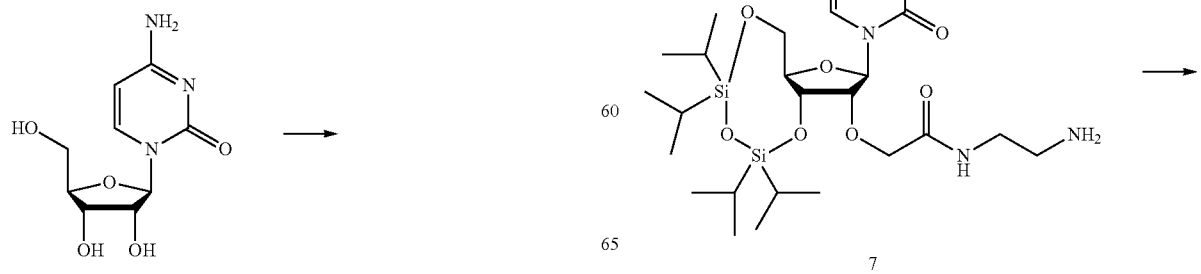

-continued

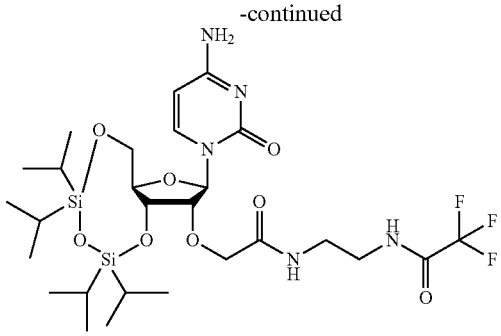

8

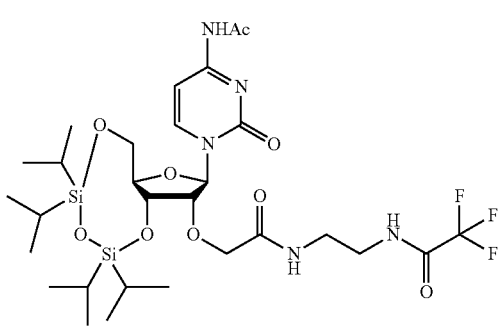

9

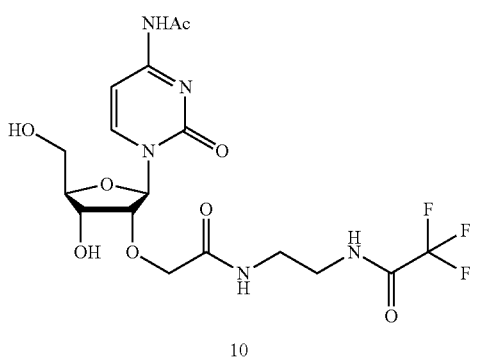

10

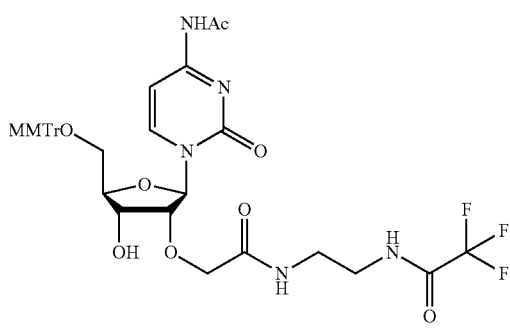

11

Example 3

Modified 2-Aminoadenosine Derivatives

Synthesis of the AECM-2-aminoadenosine derivative N$^2$,N$^6$-Diacetyl-5'-O-(4-monomethoxytrityl)-2'-O—(N-(trifluoro-acetamidoethyl)carbamoyl)-methyl-2,6-diaminopurin-9-yl riboside (16) being a precursor for 2'-O-aminoethylcarbamoylmethyl-2-aminoadenosine in oligonucleotides of the invention

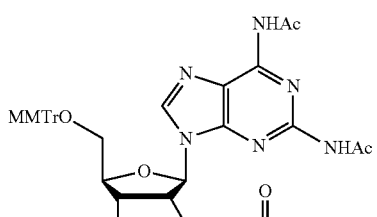

16

2'-O-(Methoxycarbonylmethylene)-2,6-diaminopurin-9-yl riboside (12)

2,6-Diaminopurin-9-yl riboside (1.13 g, 4.0 mmol) was dissolved in anhydrous DMSO (4 mL) with heating up to 70° C. and resulted solution was diluted with anhydrous DMF (16 mL). The reaction mixture was chilled in ice-water bath, NaH (60% oil dispersion, 0.28 g, 7.0 mmol) was added, and the reaction mixture was stirred for 1 h. The ice-water bath was removed and the reaction mixture was stirred for another 1 h. The suspension was chilled to −40° C. in an CH$_3$CN—CO$_2$(s) bath, and methyl 2-bromoacetate (0.66 mL, 7.0 mmol) was added dropwise. The reaction mixture was allowed to slowly warm up to ambient temperature over 2 h and then stirred for another 24 h. Glacial acetic acid (0.47 mL) was added dropwise at room temperature and the solvent was evaporated in vacuo. The residue was subjected to column chromatography using 0 to 10% CH$_3$OH in CH$_2$Cl$_2$ as eluent to give compound 12 (0.8 g, 2.26 mmol, 56%). R$_f$=0.5 (CH$_2$Cl$_2$/CH$_3$OH 4:1 v/v) (Ref: Prakash T. P. et al. *J. Med. Chem.* 2008, 51, 2766-2776).

2'-O—((N-aminoethyl)carbamoyl)methyl-2,6-diaminopurin-9-yl riboside (13)

Compound 12 (0.25 g, 0.71 mmol) was suspended in anhydrous methanol (7 mL) and ethylenediamine (0.47 mL, 7.06 mmol) was added at room temperature and the reaction mixture was stirred for 20 h. Volatiles were evaporated in vacuo and co-evaporated with toluene-methanol mixture to afford crude 10 with yield more than 95%, R$_f$=0.25 (EtOAc/CH$_3$OH/AcOH/H$_2$O 10:2:2:1 v/v), which was used for the next step without purification.

2'-O—(N-(Trifluoroacetamidoethyl)carbamoyl) methyl-2,6-diaminopurin-9-yl riboside (14)

Ethyl trifluoroacetate (0.143 mL, 1.20 mmol) was added to a solution of 13 (0.092 g, 0.24 mmol) in anhydrous methanol (1.5 mL) and the reaction mixture was stirred at room temperature for 20 h. Volatiles were evaporated in vacuo and the residue was purified via flash chromatography using 0 to 20% CH$_3$OH in CH$_2$Cl$_2$ as eluent to afford compound 14 (0.096 g, 0.20 mmol, 84% after two steps). R$_f$=0.38 (CH$_2$Cl$_2$/CH$_3$OH 4:1 v/v).

N$^2$,N$^6$-Diacetyl-5'-O-(4-monomethoxytrityl)-2'-O—(N-(trifluoroacetamidoethyl)-carbamoyl)methyl-2,6-diaminopurin-9-yl riboside (16)

Compound 14 (0.05 g, 0.104 mmol) was dried by evaporation of added anhydrous pyridine and dissolved in 1 mL of the same solvent. The solution was chilled in an ice-water bath, and acetyl chloride (0.036 mL, 0.50 mmol) was added drop wise under a nitrogen atmosphere. The reaction mixture was allowed to warm to ambient temperature and stirred for 19 h. The reaction was quenched with saturated aqueous NaHCO$_3$ and the mixture was extracted with ethyl acetate. The organic phase was dried over Na$_2$SO$_4$, filtered and concentrated under reduced pressure. The residue was re-dissolved in 2.1 mL of pyridine/ethanol (7:5 v/v) and the resulting solution was chilled in an ice-water bath. To this solution ice-cold 1 M aqueous potassium hydroxide (0.44 ml) was added, and the reaction mixture was stirred for 1 min. The pH of the solution was adjusted to pH 7 with Dowex 50WX8-200 (H$^+$). The resin was filtered off, washed with a mixture of pyridine/ethanol/water (7:5:5 v/v/v), and the filtrate was concentrated under reduced pressure to give crude 15. The residue was dried by evaporation of added anhydrous pyridine and dissolved in 1.5 mL of anhydrous pyridine/DMF (1:2 v/v) mixture. To the resulting solution triethylamine (0.022 mL, 0.157 mmol) was added followed by the addition of 4-methoxytritylchloride (0.161 g, 0.522 mmol), and the reaction mixture was stirred at ambient temperature for 3 days under a nitrogen atmosphere. The reaction was quenched with saturated aqueous NaHCO$_3$ and the mixture was extracted with ethyl acetate. The organic phase was washed with water, dried over Na$_2$SO$_4$, filtered and concentrated under reduced pressure. The residue was subjected to column chromatography using 0 to 10% CH$_3$OH in CH$_2$Cl$_2$ as eluent to give compound 16 (0.046 g, 0.055 mmol, 53% after two steps). R$_f$=0.47 (CH$_2$Cl$_2$/CH$_3$OH 9:1 v/v).

$^1$H NMR (400 MHz, CD$_3$OD): δ=8.32 (s, 1H), 7.40-7.34 (m, 4H), 7.28-7.13 (m, 8H), 6.76 (d, J=8.9 Hz, 2H), 6.26 (d, J=2.6 Hz, 1H), 4.77 (dd, J=6.7, 5.2 Hz, 1H), 4.70 (dd, J=5.1, 2.6 Hz, 1H), 4.34-4.23 (m, 3H), 3.73 (s, 3H), 3.53-3.46 (m, 1H), 3.43-3.34 (m, 5H), 2.36 (s, 3H), 2.24 (s, 3H) ppm.

Scheme 3. Synthesis of the AECM-2-aminoadenosine derivative 16.

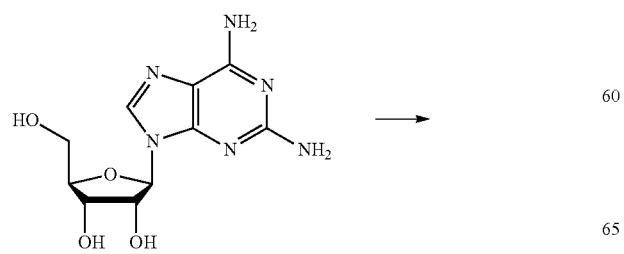

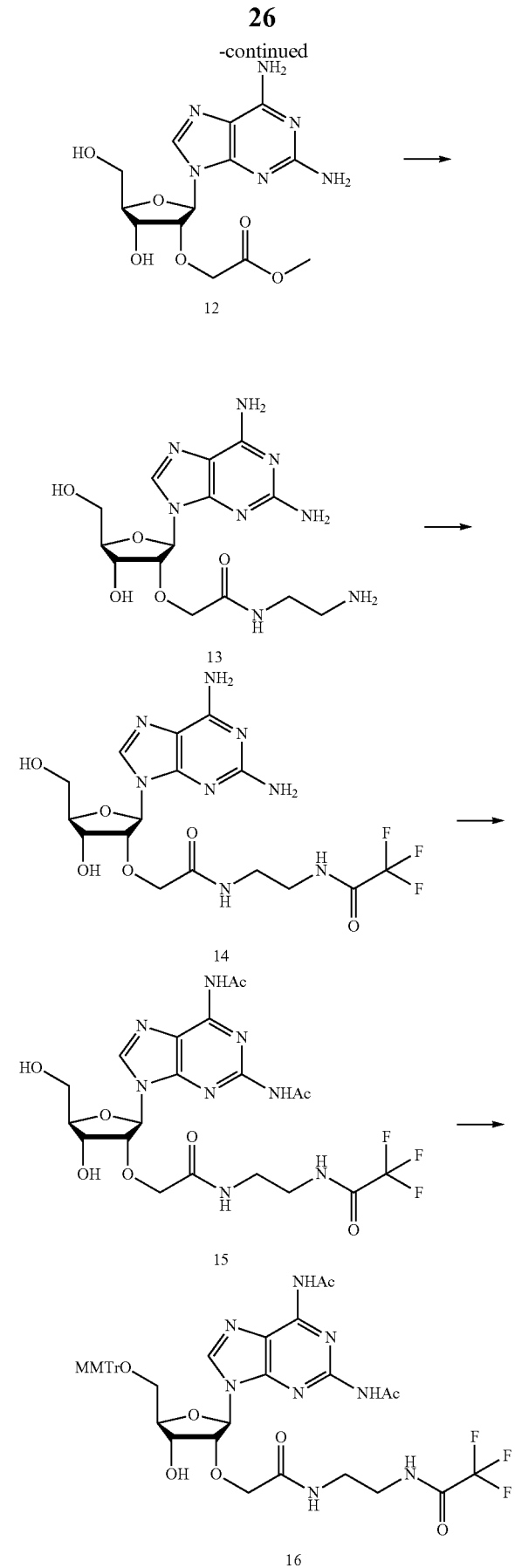

Example 4

Modified Guanosine Derivatives

Synthesis of the AECM-guanosine derivative of 5'-O-(4-Mono-methoxytrityl)-$N^2$-(Phenoxyacetyl)-2'-O—(N-(trifluoroacetamidoethyl)-carbamoyl) methylguanosine (20) being a precursor for 2'-O-aminoethylcarbamoylmethylguanosine in oligonucleotides of the invention

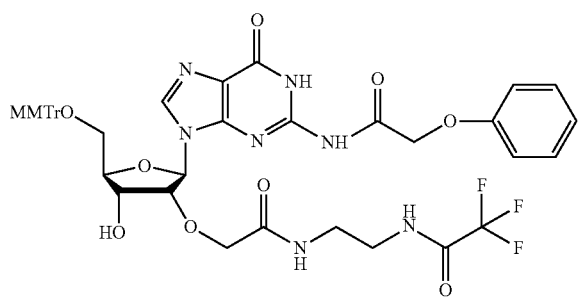

2'-O—((N-aminoethyl)carbamoyl)methylguanosine (17)

A solution of 13 (0.15 g, 0.39 mmol) in Milli-Q water (6.8 mL, pH 7.5) was incubated with adenosine deaminase (3.0 µL (3 units) of aqueous glycerol solution, 151 units/mg protein, 11 mg/mL) at room temperature for 48 h, which gave quantitative conversion to 17. The resulting mixture was freeze-dried to give compound 17. $R_f$=0.17 (EtOAc/CH$_3$OH/AcOH/H$_2$O 10:2:2:1 v/v).

2'-O—(N-(Trifluoroacetamidoethyl)carbamoyl) methylguanosine (18)

Ethyl trifluoroacetate (0.43 mL, 3.65 mmol) was added to suspension of crude 17 (0.14 g, 0.365 mmol) in anhydrous methanol (7.2 mL) and the reaction mixture was stirred at room temperature for 24 h. Volatiles were evaporated in vacuo and dried by evaporation of added methanol to give crude compound 18 (0.15 g, with purity 90%). $R_f$=0.25 (CH$_2$Cl$_2$/CH$_3$OH 4:1 v/v).

$N^2$-(Phenoxyacetyl)-2'-O—(N-(trifluoroacetamidoethyl)carbamoyl)methylguanosine (19)

Crude compound 18 (0.14 g, 0.292 mmol, recalculated from 17 as a theoretical amount) was dried, by evaporation of added anhydrous pyridine, and dissolved in 7.2 mL of the same solvent. To the resulting solution chlorotrimethylsilane (0.23 mL, 1.82 mmol) was added dropwise and the reaction mixture was stirred at ambient temperature for 3 h under nitrogen atmosphere. Phenoxyacetic anhydride (0.157 g, 0.547 mmol) was added and the reaction was kept at room temperature for 22 h. The reaction mixture was cooled in ice-water bath and water (1.3 mL) was added, and the resulted mixture was allowed to stir at room temperature overnight. The reaction mixture was partitioned between water and EtOAc. The aqueous layer was extracted with EtOAc (few drops of pyridine was added to prevent precipitation in the organic layer). Combined organic phase was dried over Na$_2$SO$_4$, filtered and concentrated under reduced pressure. The residue was subjected to column chromatography using 0 to 12% CH$_3$OH in CH$_2$Cl$_2$ as eluent to give compound 19 (0.15 g, 0.244 mmol, 84% after 4 steps). $R_f$=0.61 (CH$_2$Cl$_2$/CH$_3$OH 4:1 v/v).

5'-O-(4-Monomethoxytrityl)-$N^2$-(phenoxyacetyl)-2'-O—(N-(trifluoroacetamidoethyl)carbamoyl)-methylguanosine (20)

Compound 19 (0.046 g, 0.075 mmol) was dried by evaporation of added anhydrous pyridine (2 times) and dissolved in 1.2 mL of anhydrous DMF-DMSO-pyridine (2:1:1) mixture. To the resulting solution triethylamine (0.031 mL, 0.225 mmol) was added followed by the addition of 4-methoxytritylchloride (0.116 g, 0.375 mmol), and the reaction mixture was stirred at ambient temperature for 19 h. The reaction was quenched with saturated aqueous NaHCO$_3$ and mixture was extracted with ethyl acetate. The organic phase was washed with water, dried over Na$_2$SO$_4$, filtered and concentrated under reduced pressure. The residue was subjected to column chromatography using 0 to 10% CH$_3$OH in CH$_2$Cl$_2$ as eluent to give compound 20 (0.051 g, 0.057 mmol, 77%). $R_f$=0.53 (CH$_2$Cl$_2$/CH$_3$OH 9:1 v/v). $^1$H NMR (400 MHz, CD$_3$OD): δ=8.07 (s, 1H), 7.44-7.38 (m, 4H), 7.32-7.15 (m, 10H), 7.03-6.96 (m, 3H), 6.80 (d, J=8.8 Hz, 2H), 6.12 (d, J=2.6 Hz, 1H), 4.78 (s, 2H), 4.59-4.54 (m, 1H), 4.49 (dd, J=4.9, 2.7 Hz, 1H), 4.30 (ABq, J=15.5 Hz, 2H), 4.27-4.22 (m, 1H), 3.74 (s, 3H), 3.47-3.34 (m, 6H) ppm.

Scheme 4. Synthesis of AECM-guanosine derivative 20

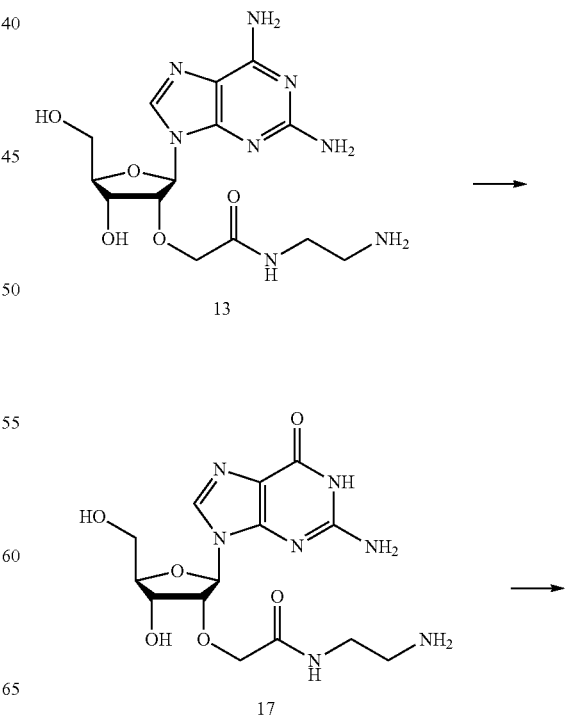

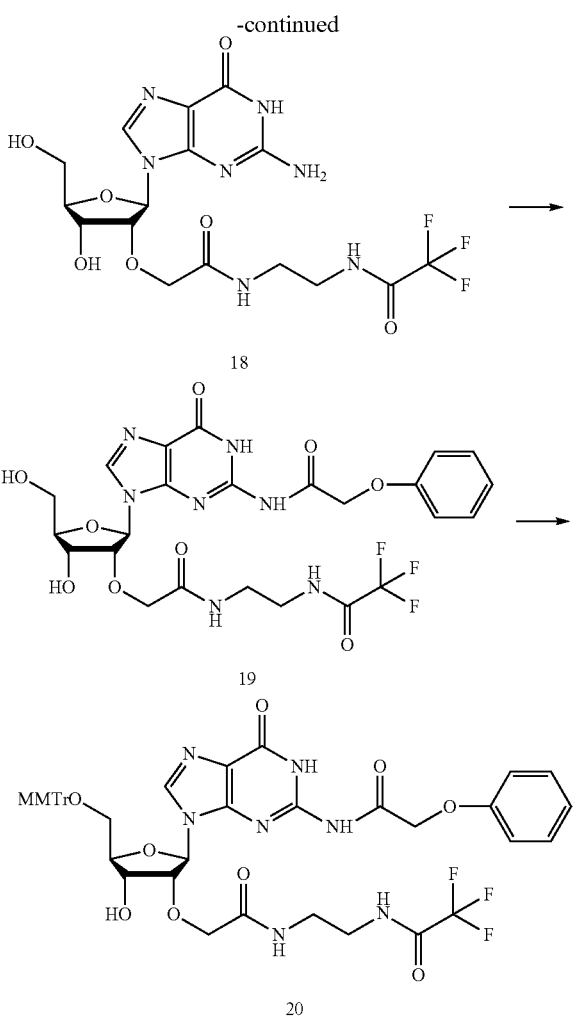

Example 5

Modified Uridine Derivatives

Synthesis of the AECM-uridine derivative 5'-O-(4-Monomethoxytrityl)-2'-O—[(N-(trifluoroacetamidoethyl)carbamoyl)methyl]uridine (27) being a precursor for 2'-O-aminoethylcarbamoylmethyl-5-methyluridine in oligonucleotides of the invention

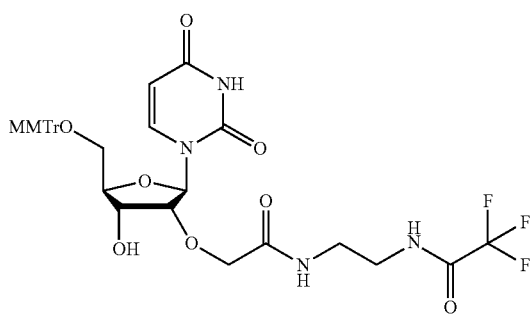

$N^3$-Pivaloyloxymethyl-3',5-O-(1,1,3,3-tetraisopropyl-1,3-disiloxanediyl)uridine

(21) was synthesized according to a reported procedure (ref: Kachalova, A., et al. *Org. Biomol. Chem.*, 2004, 2, 2793-2797).

2'-O—(O-Methylcarboxymethyl)-$N^3$-pivaloyloxymethyl-3',5'-O-(1,1,3,3-tetraisopropyl-1,3-disiloxanediyl)uridine (22)

Compound 21 (6.98 g, 11.62 mmol) was dried by evaporation of added anhydrous acetonitrile (2 times) and dissolved in 120 mL of the same solvent. Methyl 2-bromoacetate (1.43 mL, 15.11 mmol) was added dropwise to the stirred solution under a nitrogen atmosphere followed by the addition of the phosphazene base, tert-Butylimino-tri(pyrrolidino)phosphorane, (BTPP, 4.97 mL, 16.27 mmol). The reaction mixture was stirred at ambient temperature for 2 h. Volatiles were evaporated to dryness in vacuo and the residue was dried by evaporation of added toluene. The crude product was purified via flash chromatography using 0 to 25% EtOAc in hexane as eluent to afford compound 22 (7.19 g, 10.68 mmol, 92%). $R_f$=0.63 (EtOAc/toluene 3:7 v/v).

2'-O—(O-Methylcarboxymethyl)-$N^3$-pivaloyloxymethyluridine (23)

To a solution of compound 22 (6.96 g, 10.34 mmol) in 90 mL of anhydrous tetrahydrofuran triethylamine trihydrofluoride (4.04 mL, 24.82 mmol) was added under a nitrogen atmosphere and the reaction mixture was stirred at room temperature for 2 h. Volatiles were evaporated in vacuo and the residue was dried by evaporation of added methanol and $CH_2Cl_2$. The crude product was purified via flash chromatography using 0 to 6% $CH_3OH$ in $CH_2Cl_2$ as eluent to afford compound 23 (4.18 g, 9.71 mmol, 94%). $R_f$=0.59 ($CH_2Cl_2/CH_3OH$ 9:1 v/v).

2'-O—[(N-(trifluoroacetamidoethyl)carbamoyl)methyl]uridine (26)

Ethylenediamine (3.17 mL, 47.50 mmol) was added to a solution of compound 23 (4.09 g, 9.50 mmol) in 65 mL of anhydrous methanol at room temperature and the reaction mixture was stirred for 20 h. Volatiles were evaporated in vacuo and the residue was dried by evaporation of added toluene-methanol and $CH_2Cl_2$ to give crude intermediate 24. This crude compound was treated with 25% aqueous ammonia (120 mL) at ambient temperature for 20 h. Water was partially removed under reduced pressure, where after lyophilization resulted in isolation of crude 25. The intermediate 25 was then dissolved in anhydrous methanol (90 mL) and ethyl trifluoroacetate (13.8 mL, 116.20 mmol) was added at room temperature and the reaction mixture was stirred for 23 h. Volatiles were evaporated in vacuo and the residue was purified via flash chromatography using 0 to 16% $CH_3OH$ in $CH_2Cl_2$ as eluent to afford compound 26 (2.51 g, 5.70 mmol, 60% after three steps). $R_f$=0.57 ($CH_2Cl_2/CH_3OH$ 4:1 v/v).

5'-O-(4-Monomethoxytrityl)-2'-O—[(N-(trifluoroacetamidoethyl)carbamoyl)-methyl]uridine (27)

Compound 26 (2.22 g, 5.04 mmol) was dried by evaporation of added anhydrous pyridine (2 times) and dissolved in 50 mL of anhydrous DMF-pyridine (3:2) mixture. To the resulting solution 4-methoxytritylchloride (1.87 g, 6.05 mmol) was added under a nitrogen atmosphere and the reaction mixture was stirred at ambient temperature for 24 h. Solvents were partially removed under reduced pressure and a cold saturated aqueous NaHCO$_3$ solution was added to the residue and the mixture was extracted with ethyl acetate. The organic phase was washed with water, dried over Na$_2$SO$_4$, filtered and concentrated under reduced pressure. Traces of pyridine were removed by evaporation of added toluene. The crude product was subjected to column chromatography using 0 to 10% CH$_3$OH in CH$_2$Cl$_2$ as eluent to give compound 27 (2.98 g, 4.18 mmol, 83%). R$_f$=0.54 (CH$_2$Cl$_2$/CH$_3$OH 9:1 v/v). $^1$H NMR (400 MHz, CD$_3$OD): δ=8.05 (d, J=8.1 Hz, 1H), 7.47-7.40 (m, 4H), 7.35-7.22 (m, 8H), 6.88 (d, J=8.9 Hz, 2H), 5.88 (d, J=1.1 Hz, 1H), 5.20 (d, J=8.1 Hz, 1H), 4.51 (dd, J=8.6, 5.1 Hz, 1H), 4.29 (ABq, J=15.7 Hz, 2H), 4.17-4.10 (m, 1H), 4.03 (dd, J=5.1, 1.1 Hz, 1H), 3.78 (s, 3H), 3.56-3.50 (m, 2H), 3.46-3.42 (m, 4H) ppm.

Scheme 5. Synthesis of the AECM-uridine derivative 27.

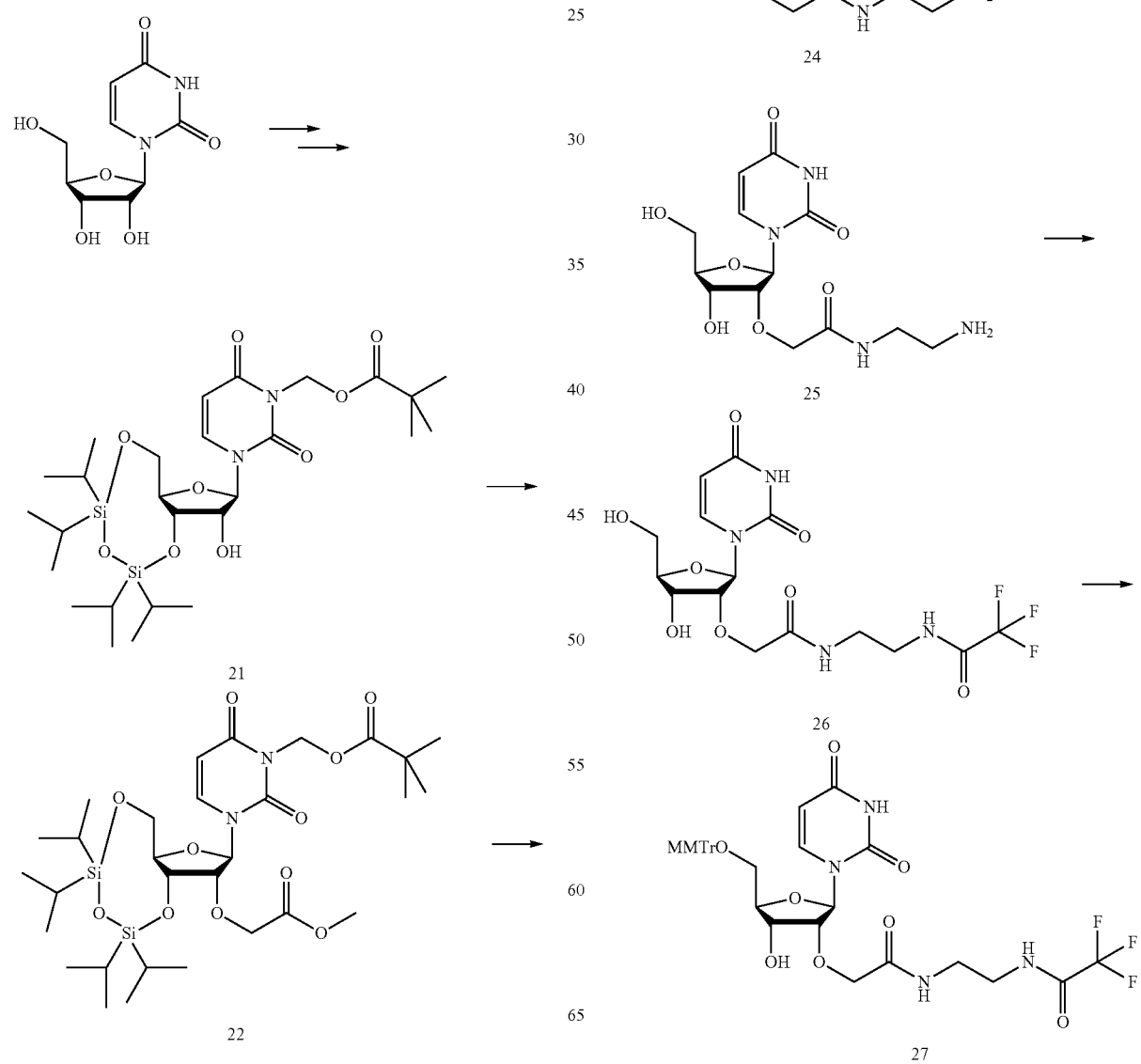
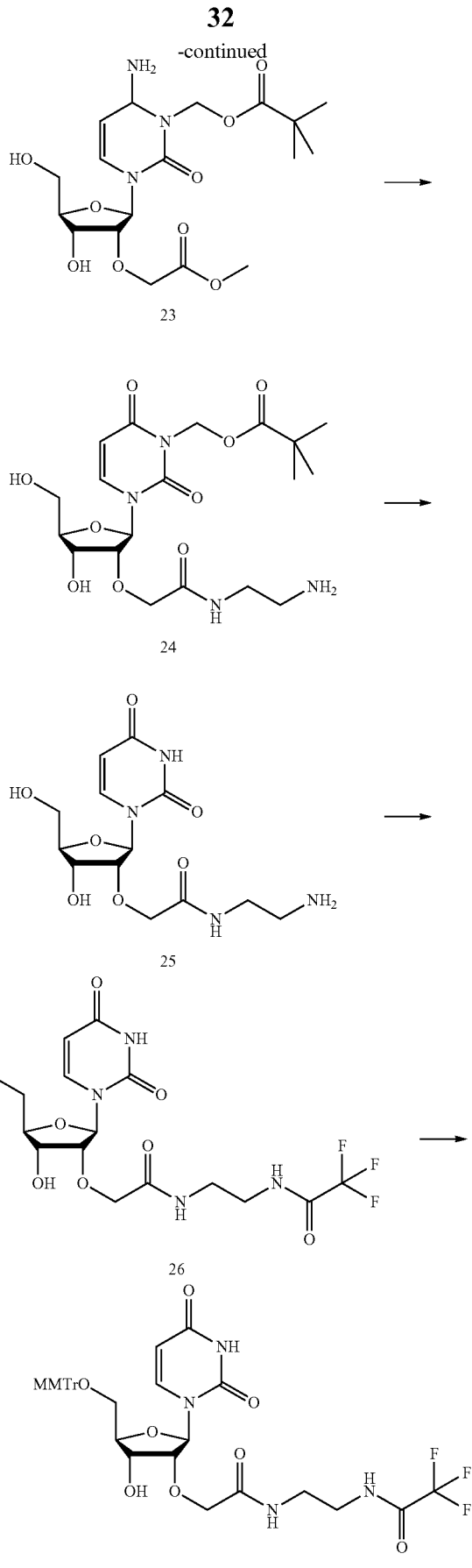

Example 6

Modified Adenosine Derivatives

Synthesis of the AECM-adenosine derivative 5'-O-(4-Monomethoxytrityl)-2'-O—(N-(trifluoroacetamidoethyl)-carbamoyl)methyl-$N^6$-butyryladenosine 3'-H-phosphonate triethylammonium salt (30) being a precursor for 2'-O-aminoethylcarbamoylmethyladenosine in oligonucleotides of the invention

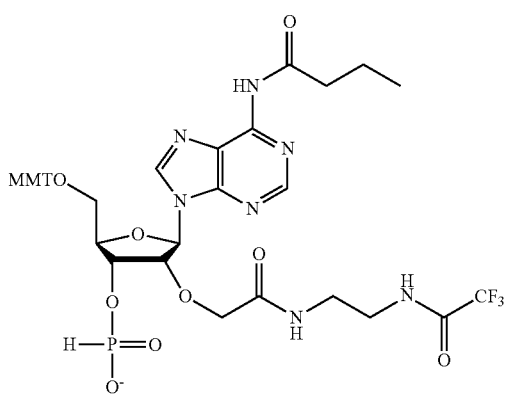

30

5'-O-(4-monomethoxytrityl)-2'-O—(N-(trifluoroacetamidoethyl)carbamoyl)-methyl-$N^6$-butyryladenosine (29)

Compound 2 (235 mg, 0.32 mmol) was dried by evaporation of added pyridine (dried over 4 Å molecular sieves) and dissolved in dry pyridine. To the solution trimethylsilyl chloride (TMS-Cl, 123 µl, 0.96 mmol) was added. The reaction was then left stirring for 1 h at room temperature. The solution was then chilled to −10° C. (ice-salt bath) and butyric anhydride (64 µl, 0.39 mmol) was added. The reaction was left over night. Removal of solvent under reduced pressure yielded the crude product which was chromatographed on silica gel using $CH_2Cl_2$/methanol (20:1) as eluent yielding 169 mg (60%) of 28 as a white foam. [$^1$H-NMR ($CDCl_3$): 0.05 (s, 9H, Si-Me); 1.00 (t, 3H, $CH_3$—Bu); 1.75 (m, 2H, $CH_2$—Bu); 2.80 (m, 2H, $CH_2$-Bu); 3.25 and 3.50 (d, 2H, 5H'); 3.40 (m, 4H, $CH_2$-ethylene); 3.75 (s, 3H, $CH_3$-trityl); 4.10-4.25 (d, 2H, $CH_2$-carbamoyl); 4.25 (m, 1H, 4H'); 4.50 (m, 2H, 3H' and 4H'); 6.15 (d, 1H, H1'); 6.75 (d, 2H, trityl); 7.15-7.50 (m, 12H, trityl); 8.25 (s, 1H, H2-base); 8.65 (s, 1H, H8-base).] Compound 28 (0.085 mmol, 75 mg) was dissolved in 5 ml $CH_2Cl_2$ (dried over 4 Å molecular sieves) and three drops of triethylamine-trihydrofluoride was added to the solution under stirring. After 20 minutes TLC showed that the reaction was complete. The solution was washed with 5 ml brine where the pH had been calibrated to 8.0 with a saturated $NaHCO_3$ solution. Removal of solvent from the organic layer under reduced pressure yielded 68 mg (99%) of the product 29 as a white foam. $^1$H-NMR ($CDCl_3$): 1.00 (t, 3H, $CH_3$—Bu); 1.75 (m, 2H, $CH_2$—Bu); 2.80 (m, 2H, $CH_2$—Bu); 3.30-3.55 (m, 6H, 5H'+$CH_2$-ethylene); 3.75 (s, 3H, $CH_3$-trityl); 4.10-4.30 (d, 2H, $CH_2$-carbamoyl); 4.35 (m, 1H, 4H'); 4.50-75 (m, 2H, 3H' and 4H'); 6.20 (d, 1H, H1'); 6.75 (d, 2H, trityl); 7.20-7.50 (m, 12H, trityl); 8.25 (s, 1H, H2-base); 8.65 (s, 1H, H8-base).

5'-O-(4-monomethoxytrityl)-2'-O—(N-(trifluoroacetamidoethyl)-carbamoyl)methyl-$N^6$-butyryladenosine 3'-H-phosphonate triethylammonium salt (30)

Imidazole (265 mg, 3.95 mmol) was dissolved in 35 ml $CH_2Cl_2$ (dried over 4 Å molecular sives). The solution was chilled to −10° C. and $PCl_3$ (116 µl, 1.26 mmol) was added followed by triethylamine (560 µl, 4.04 mmol) whereupon the solution were cooled down further to −78° C. Compound 29 (285 mg, 0.359 mmol) was dissolved in 3 ml dry $CH_2Cl_2$. The solution containing compound 29 was then slowly added with a syringe through a septa into the chilled $PCl_3$/Imidazole solution. The mixture was then left for 2 h during which time the mixture was allowed to reach room temperature. The mixture was then extracted with $CH_2Cl_2$ (15 ml) and was twice washed with 30 ml 2M aqueous triethylammonium bicarbonate and the collected organic layer was dried with $Na_2SO_4$ and concentrated. Removal of solvent under reduced pressure yielded 345 mg (99%) of 30 as a white foam. $^1$H-NMR ($CDCl_3$): 1.00-1.10 (t, 3H, $CH_3$—Bu); 2.75-2.85 (m, 2H, $CH_2$—Bu); 3.75-3.85 (m, 2H, $CH_2$—Bu); 3.25-3.65 (m, 6H, 5H'+2*$CH_2$-ethylene); 3.75 (s, 3H, $CH_3$-trityl); 3.85-4.10 (d, 2H, $CH_2$-carbamoyl); 4.30 (d, 1H, 4H'); 4.80 (m, 1H, 2H'); 5.00 (m, 1H, 3H'); 6.10 and 7.75 (d, 1H, PH); 6.15 (d, 1H, H1'); 6.75 (d, 2H, trityl); 7.20-7.45 (m, 12H, trityl); 8.10 (s, 1H, H2-base); 8.60 (s, 1H, H8-base). 31P-NMR: 3.5 ppm. ES-TOF): m/z calculated for M−, 868.27. found: 868.27.

Scheme 6 Synthesis of AECM-adenosine derivative 30

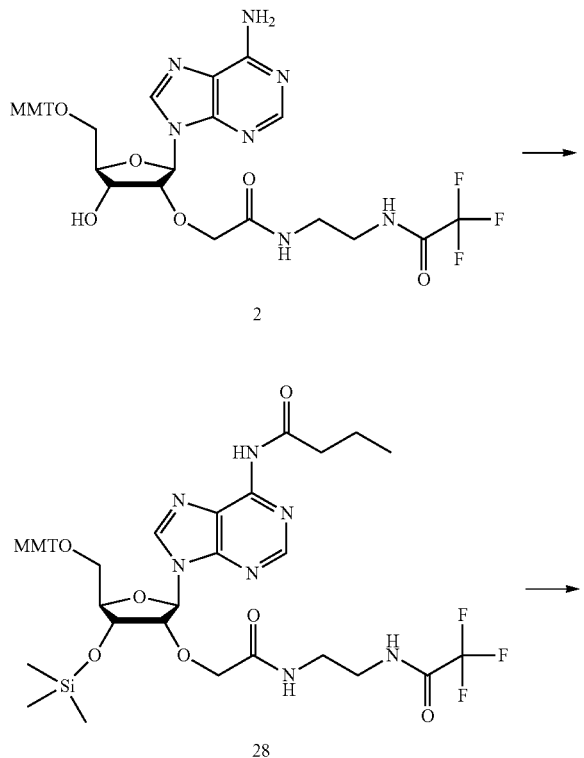

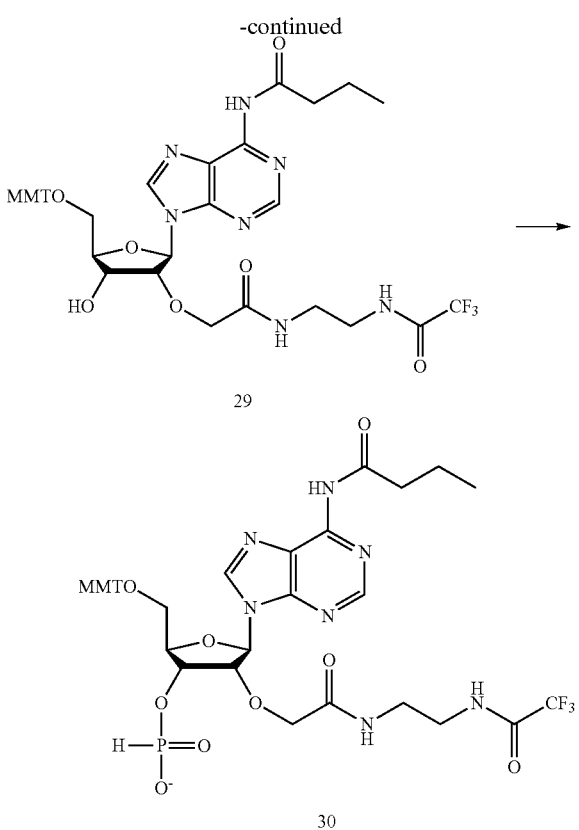

29

30

Example 7

Synthesis of 2'-O-AECM modified oligonucleotides (O1-O4) and non-modified oligonucleotides (dO1-dO4)

The oligonucleotides with SEQ ID Nos 1-8 were synthesized on an Applied Biosystems 392A DNA/RNA synthesizer. Monomers for the solid-phase synthesis were dried in vacuo in the presence of $CaH_2$ prior to use. Oligonucleotides were assembled on pre-loaded CPG cartridges using 2-cyanoethyl phosphoramidite chemistry compound 4 and commercial reagents [5'-DMT-dN-3'-P(OCE)NiPr$_2$] dN=dU, dA$^{Bz}$, dC$^{Ac}$, dG$^{iPrPac}$, in a 1.0 μmol scale using the manufacturer's protocols and 10 min coupling time. For the detritylation step after coupling with compound 4 an extra round of 1 minute acid treatment was used. After synthesis the resin was transferred from the cartridge to a tightly sealed container and treated with 2 ml ethylenediamine solution (20% in methanol) for 24 h at room temperature. The CPG-resin was then removed by filtration and washed with 4 ml methanol and 4 ml $H_2O$. The filtrate was evaporated under reduced pressure at 40° C. and further dried by twice evaporating added ethanol (99.8%. 3 ml). $H_2O$ was added and the crude oligonucleotide product was lyophilized. The oligonucleotides were then purified with RP HPLC using an ODS Hypersil (250×10 mm, 5 μm) column. A flow rate of 4 ml/min and a temperature of 50° C. was used. First 100% buffer A was flushed through for 3 min, then a linear gradient of 0-50% buffer B over 40 min was used. Buffer A: 50 mM triethylammonium acetate in water (pH 6.5); Buffer B: 50 mM triethylammonium acetate (pH 6.5) in 50% aqueous acetonitrile. The oligonucleotides were lyophilized three times before use and stored frozen.

MS (ES-TOF) [M-H]$^-$ mass of the Oligos: O1: $C_{187}H_{245}N_{86}O_{106}P_{16}{}^-$=5889. found, 5890; O2: $C_{178}H_{236}N_{89}O_{95}P_{14}{}^-$=5576. found, 5577; O3: $C_{154}H_{211}N_{71}O_{83}P_{12}{}^-$=4756. found, 4758; O4: $C_{178}H_{251}N_{89}O_{87}P_{12}{}^-$=5401. found, 5402.

Example 8

Synthesis of the fluorescein labelled 2'-O-AECMA$_{10}$ and dA$_{10}$ oligonucleotides (O5 and dO5)

The oligonucleotides with SEQ ID Nos 9-10 were synthesized on an Applied Biosystems 392A DNA/RNA synthesizer. Monomers for the solid-phase synthesis were dried in vacuo in the presence of $CaH_2$ prior to use. Oligonucleotides were assembled on pre-loaded CPG cartridges 3'-(6-Fluorescein)-CPG purchased from Glen Research, using 2-cyanoethyl phosphoramidite chemistry and compound 4 and N$^6$-benzoyl-5'-O-DMT-dA-3'-P(OCE)NiPr$_2$ (also from Glen Research) respectively at 1.0 μmol scale using the manufacturers protocols (and 1 min additional acid treatment after coupling with 4, as above) with 10 min coupling time. After synthesis the resin was transferred from the cartridge and treated with 2 ml ethylenediamine solution (20% in methanol) for 24 h at room temperature in a tightly sealed flask. The CPG resin was then removed by filtration and washed with approximately 4 ml methanol and 4 ml $H_2O$. The filtrate was evaporated under reduced pressure at 40° C. and dried by twice evaporating added ethanol (99.8%, 3 ml). $H_2O$ was added and the crude oligonucleotides were lyophilized. The oligonucleotides were then purified with RP HPLC using an ODS Hypersil (250×10 mm, 5 μm) column. A flow rate of 4 ml/min and a temperature of 50° C. was used. First 100% buffer A was flushed through for 3 min, then a linear gradient of 0-50% buffer B over 40 min was used. Buffer A: 50 mM triethylammonium acetate in water (pH 6.5); Buffer B: 50 mM triethylammonium acetate (pH 6.5) in 50% aqueous acetonitrile. The oligonucleotides were lyophilized three times before use and stored frozen. MS (ES-TOF) [M-H]$^-$ mass of the Oligos: dA$_{10}$ calculated for $C_{128}H_{146}N_{51}O_{58}P_{10}{}^-$=3637. found, 3637; 2'-O-AECMA$_{10}$: calculated for $C_{168}H_{226}N_{71}O_{78}P_{10}{}^-$=4798. found, 4798.

Example 9

Thermal Melting Analysis of Duplexes of Modified Oligonucleotides, Compared with Corresponding Non-Modified Nucleotides Absorbance vs. temperature profiles were measured at 260 nm on a Cary 300 UV/VIS dual beam spectrophotometer (Varian) equipped with a programmable thermo electrical temperature controlled 6×6 sample holder. Extinction coefficients were calculated by the nearest-neighbour approximation. Melting temperatures were measured with 1:1 molar mixtures of oligonucleotide and the corresponding target RNA or DNA, each at a concentration of 4 μM, in a 10 mM phosphate buffer containing 100 mM NaCl and 0.1 mM EDTA at pH 7.0. Prior to every melting experiment, the phosphate buffer was degassed on an ultra sonic bath. The samples were rapidly heated to 90° C., left for 5 min and then allowed to cool to 20° C. After equilibration for 10 min at the starting temperature, the dissociation was recorded by heating to 90° C. at rate of 0.2° C. min$^{-1}$. The Varian Cary WinUV software, version 3 was used to determine the melting temperatures ($T_m$) from the derivatives of the experimental melting curves. The results are provided in Table 1.

TABLE 1

Thermal melting (Tm) of oligonucleotides in 100 mM Na+, 10 mM phosphate, 0.1 mM EDTA, pH 7 at 4 microM strand concentration.

| SEQ ID NO | Tm (° C.) with Compl. RNA | ΔTm (° C.) per modification for Complexes with RNA | Tm (° C.) with Compl. DNA | ΔTm (° C.) per modification for Complexes with DNA |
|---|---|---|---|---|
| 1 (O1) 29.4% modifications | 61.1 | 0.5 | 60.2 | −0.3 |
| 2 (dO1) Comparative sequence | 58.4 | | 61.8 | |
| 3 (O2) 50.0% modifications | 56.6 | 2.3 | 60.0 | 1.0 |
| 4 (dO2) Comparative sequence | 40.2 | | 51.0 | |
| 5 (O3) 53.8% modifications | 44.6 | 0.9 | 46.0 | −0.1 |
| 6 (dO3) Comparative sequence | 38.6 | | 47.0 | |
| 7 (O4) 92.3% modifications | 25.3 | 1.6 | 32.7 | 0.2 |
| 8 (dO4) Comparative sequence | 5.6 | | 30.0 | |

Example 10

Figure 2:
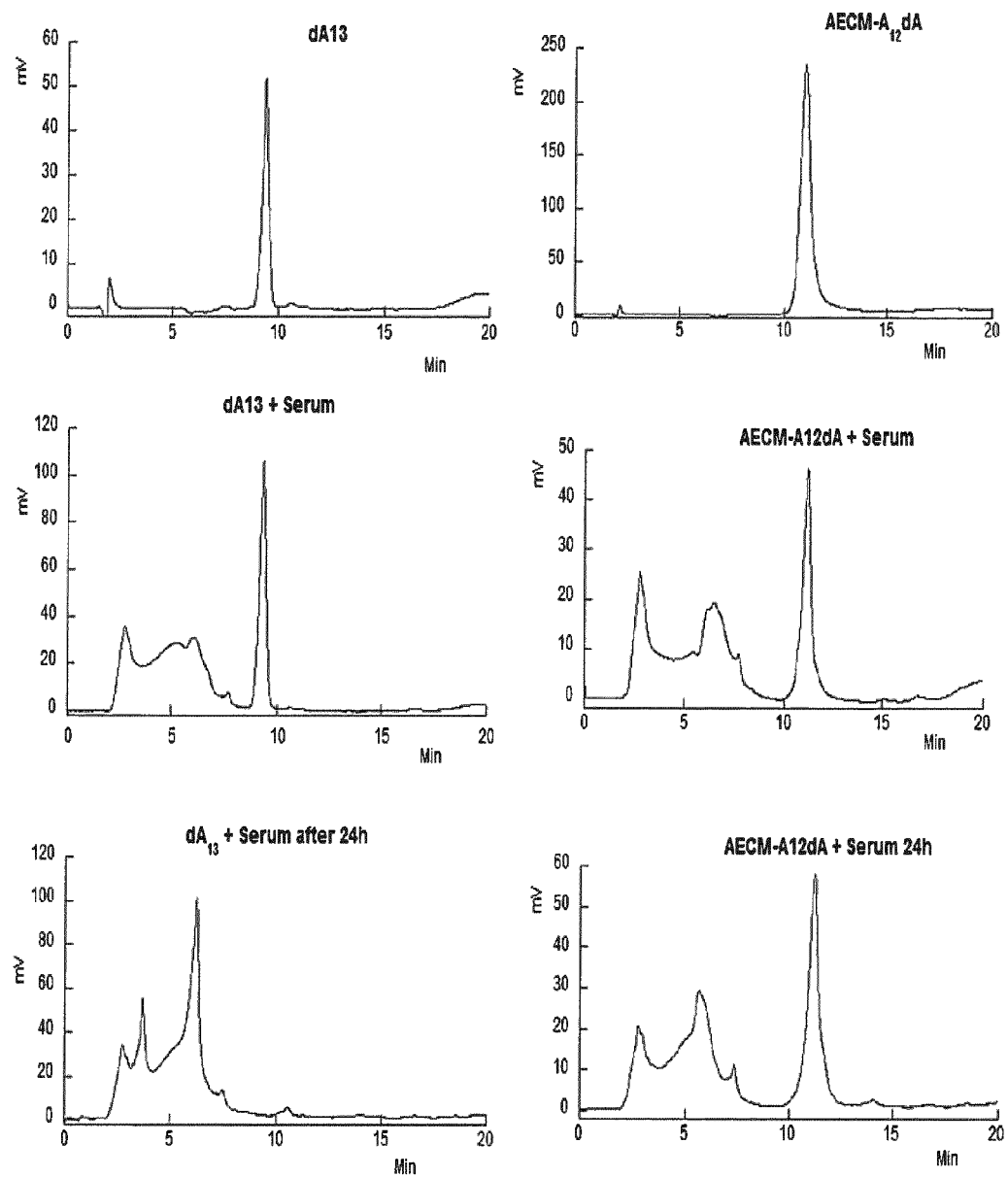
FIG. 2 provides chromatograms showing the stability of substantially modified AECM containing oligonucleotides (SEQ ID NO 7) in human serum under conditions where a native DNA oligonucleotide (SEQ ID NO 8) is completely degraded.

Serum Stability Test with Modified Oligonucleotides, Compared with Corresponding Non-Modified Oligonucleotides The oligonucleotides of SEQ ID Nos 7 (04; AECM-$A_{12}$-dA) and 8 (dO4; $dA_{13}$) were dissolved in 0.05 mL water in an eppendorf tube and then 0.45 mL human serum (Sigma-Aldrich) was added. After mixing a 0.1 mL aliquot was immediately withdrawn diluted with 0.9 mL buffer A and a 0.1 mL aliquot thereof immediately injected for HPLC-analysis. The remaining 90% serum solution was incubated for 24 h at 37° C. whereupon another 0.1 mL aliquot was withdrawn and analyzed by HPLC (FIG. 2). RP-HPLC analysis was performed using an ODS Hypersil (250×4.6 mm, 5 μm) column. A flow rate of 0.8 ml/min and a linear gradient from 50 mM triethylammonium acetate in water (pH 6.5) to 50 mM triethylammonium acetate (pH 6.5) in 25% aqueous acetonitrile in 20 minutes was used.

The resulting chromatograms are provided in FIG. 2. The stability in human serum of a substantially modified AECM containing oligonucleotide (SEQ ID NO 7; AECM-$A_{12}$-dA) is demonstrated under conditions where the corresponding native DNA oligonucleotide (SEQ ID NO 8; $dA_{13}$) is completely degraded.

Example 11

Oligonucleotide Uptake by Cells as Visualized by Confocal Microscopy with Modified Oligonucleotides, Compared with Corresponding Non-Modified Nucleotides U20S cells (human osteosarcoma cell line) grown at 37° C., 5% CO2 were plated onto coverslips in a 24 well plate in order to have 80-90% confluency the next day. Fluorescent labelled oligonucleotides with SEQ ID NOs 9 (AECM-$A_{10}$; 100% modification) and 10 ($dA_{10}$, no modification) were diluted to specific concentrations in a final volume of 300 μl by using OPTImem. Cells were washed twice with PBS buffer and the diluted oligonucleotide was then added to the cells. After a period of incubation the cells were again washed 3 times with PBS buffer and further processed for confocal microscopy as follows: cells were fixed in 3.7% paraformaldeheyde for 25 min and washed three times with PBS buffer. The nucleus was stained with DRAQ5 (10 μM) for 4 min, 37° C. after which the cells were washed two times with PBS buffer. Finally the cell membrane was stained with WGA-Alexa555, with 30 min incubation after which the cells were again washed twice with PBS. Cells were then mounted with DAKO fluorescence mounting medium. Confocal microscopy was performed using a Zeiss LSM 510 microscope equipped with a Plan-Apochromat 63×/1.4 oil DIC objective and 0.8 aperture. Pictures were taken using a Z axis that crossed the middle section of the cell.

Figure 3:
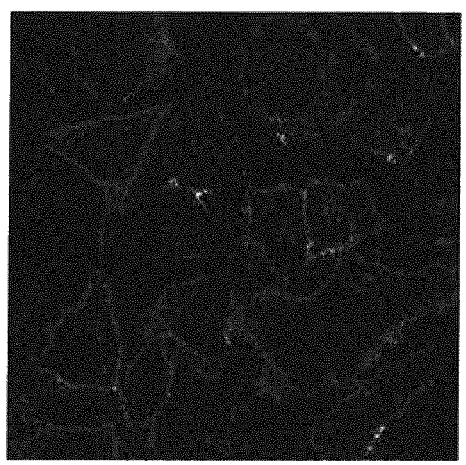
FIG. 3 provides confocal microscopy images demonstrating efficient cellular uptake of fully modified AECM containing oligonucleotides (SEQ ID NO 9) compared with a native DNA oligonucleotide (SEQ ID NO 10).
Figure 3:
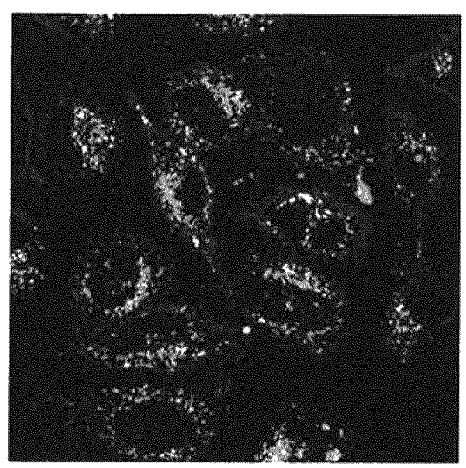
Figure 4:
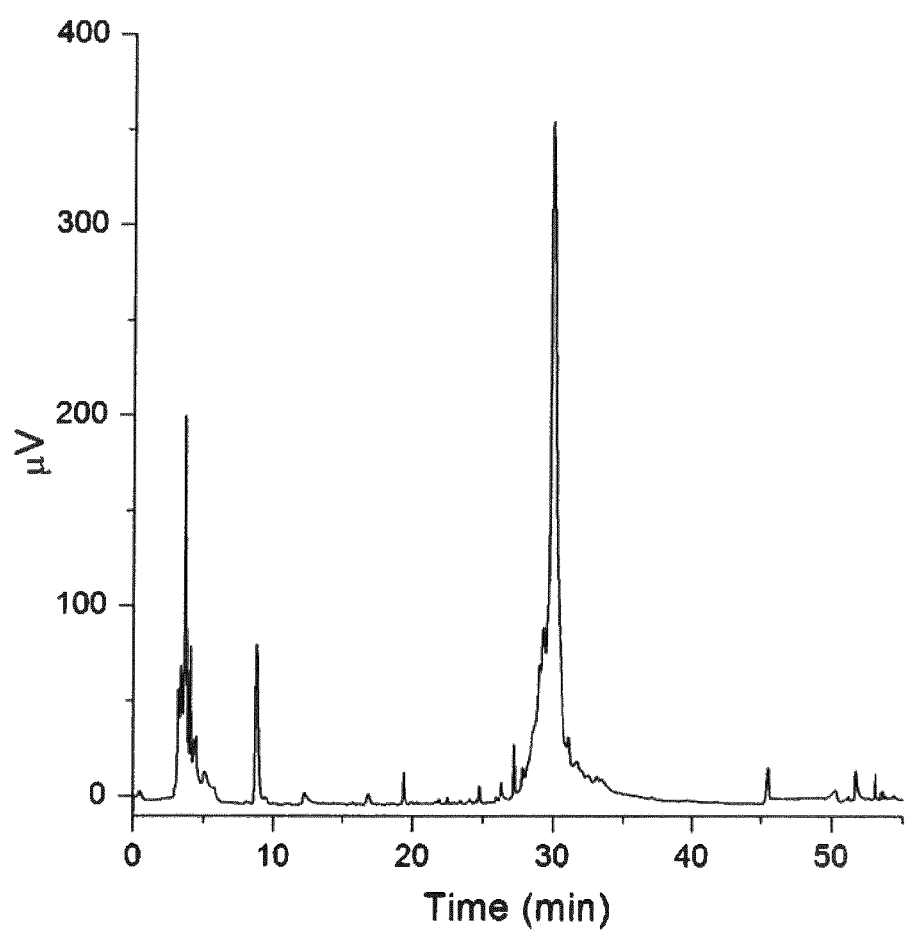
FIG. 4 provides RP-HPLC analysis of crude 18-mer CPO, i.e., fully modified AECM-oligonucleotide (SEQ ID NO 11, 5'-ccucuuaccucaguuaca) synthesized with amidite chemistry on an automated oligonucleotide synthesizer.

The resulting confocal microscopy images are provided in FIG. 3. Efficient cellular uptake of a fully modified AECM containing oligonucleotide (SEQ ID NO 9; panel B) is evident as a bright staining in the cells compared with a corresponding native DNA oligonucleotide (SEQ ID NO 10; panel A), which is not efficiently taken up by the cell.

Example 12

Synthesis of AECM-Modified Phosphoramidites of Cytidine Derivative (31), Guanosine Derivative (32), and Uridine Derivative (33)

$N^4$-Acetyl-3'-O—(N,N-diisopropylamino-(2-cyanoethoxy)phosphinyl)-5'-O-(4-methoxytrityl)-2'-O—[(N-(trifluoroacetamidoethyl)carbamoyl)methyl] cytidine (31)

To the chilled (ice bath) solution of compound 11 (2.11 g, 2.8 mmol) in 40 mL of DCM-acetonitryle (5:3 v/v) mixture N,N'-diisopropylethylamine (2.4 mL, 14 mmol) was added under nitrogen atmosphere followed by the addition of 2-cyanoethyl N,N-diisopropylphosphoramidochloridite (1.25 mL, 5.6 mmol). The reaction mixture was stirred for 30 min and after was allowed to warm to ambient temperature and stirred for 2.5 h. Methanol (1.4 mL) was added and solvents were partially removed in vacuo. The residue was partitioned between EtOAc and 10% aqueous solution of NaHCO$_3$ and the aqueous phase was washed with EtOAc. The combined organic phase was dried over Na$_2$SO$_4$, filtered and concentrated under reduced pressure. The crude product was purified by flash column chromatography using 0 to 6% CH$_3$OH in EtOAc containing 0.1% of triethylamine as eluent to give 31 (2.45 g, 92%). R$_f$=0.57 (CH$_2$Cl$_2$/CH$_3$OH 9:1 v/v). $^{31}$P NMR (162 MHz, CDCl$_3$): δ=152.5, 149.2 ppm. HRMS (ESI-TOF): calcd. for C$_{46}$H$_{54}$F$_3$N$_7$O$_{10}$P [M-H]$^-$ 952.3627. found 952.3629.

3'-O—(N,N-Diisopropylamino-(2-cyanoethoxy) phosphinyl)-5'-O-(4-methoxytrityl)-N$^2$-(phenoxyacetyl)-2'-O—[(N-(trifluoroacetamidoethyl)carbamoyl)methyl]guanosine (32)

Compound 19 (0.708 g, 0.8 mmol) was dried by co-evaporation with anhydrous THF and dissolved in 8 mL of the same solvent. To the resulted chilled (ice bath) solution N,N'-diisopropylethylamine (0.7 mL, 4 mmol) was added under nitrogen atmosphere followed by the addition of 2-cyanoethyl N,N-diisopropylphosphoramidochloridite (0.36 mL, 1.6 mmol). After 30 min the ice bath was removed and the reaction mixture was stirred for another 3 h. The reaction was quenched by the addition of the methanol (0.5 mL) and solvent was partially removed under reduced pressure. The residue was partitioned between EtOAc and 10% aqueous solution of NaHCO$_3$ and the aqueous phase was washed with EtOAc. The combined organic phase was dried over Na$_2$SO$_4$, filtered and concentrated under reduced pressure. The crude product was purified by flash column chromatography using 0 to 10% 2-propanol in dichloromethane containing 0.1% of triethylamine as eluent to give 32 (0.66 g, 76%). R$_f$=0.50 (CH$_2$Cl$_2$/CH$_3$OH 16:1 v/v). $^{31}$P NMR (162 MHz, CDCl$_3$): δ=150.1, 147.8 ppm. HRMS (ESI-TOF): calcd. for C$_{53}$H$_{58}$F$_3$N$_9$O$_{11}$P [M-H]$^-$ 1084.3951. found 1084.3955.

3'-O—(N,N-Diisopropylamino-(2-cyanoethoxy) phosphinyl)-5'-O-(4-methoxytrityl)-2'-O—[(N-(trifluoroacetamidoethyl)carbamoyl)methyl]uridine (33)

Compound 26 (1.71 g, 2.4 mmol) was dried by co-evaporation with anhydrous THF and dissolved in 24 mL of the same solvent. To the resulted chilled (ice bath) solution N,N'-diisopropylethylamine (2.09 mL, 12 mmol) was added under nitrogen atmosphere followed by the addition of 2-cyanoethyl N,N-diisopropylphosphoramidochloridite (1.07 mL, 4.8 mmol). After 30 min the ice bath was removed and the reaction mixture was stirred for another 2 h. The reaction was quenched by the addition of the methanol (1.2 mL) and solvent was partially removed under reduced pressure. The residue was partitioned between EtOAc and 10% aqueous solution of NaHCO$_3$ and the aqueous phase was washed with EtOAc. The combined organic phase was dried over Na$_2$SO$_4$, filtered and concentrated under reduced pressure. The crude product was purified by flash column chromatography using 0 to 10% acetonitrile in EtOAc containing 0.1% of triethylamine as eluent to give 33 (1.77 g, 81%). R$_f$=0.50 (CH$_2$Cl$_2$/CH$_3$OH 15:1 v/v). $^{31}$P NMR (162 MHz, CDCl$_3$): δ=152.1, 148.9 ppm. HRMS (ESI-TOF): calcd. for C$_{44}$H$_{51}$F$_3$N$_6$O$_{10}$P [M-H]$^-$ 911.3362. found 911.3361.

Scheme 7 Synthesis of the phosphoramidites of AECM-modified cytidine derivative (31), AECM-modified guanosine derivative (32), and AECM-modified uridine derivative (33).

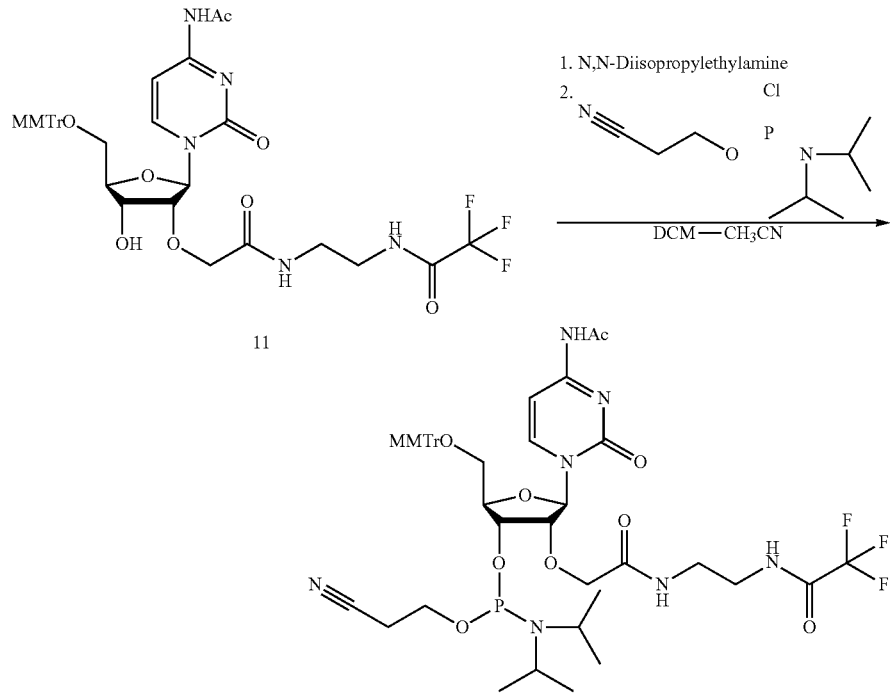

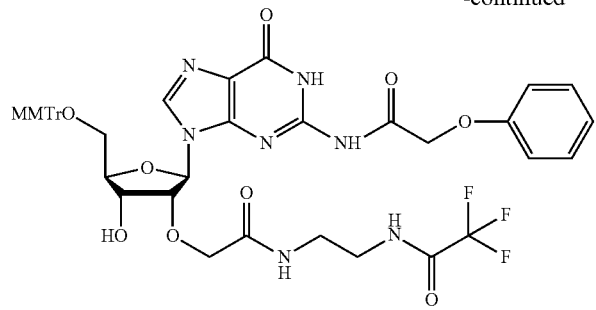

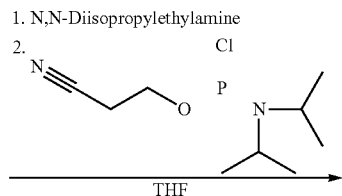

19

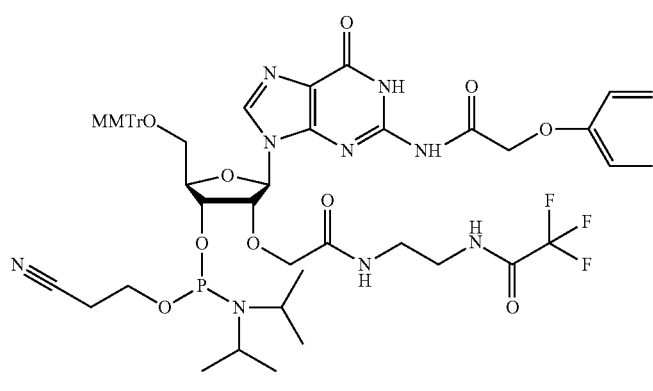

32

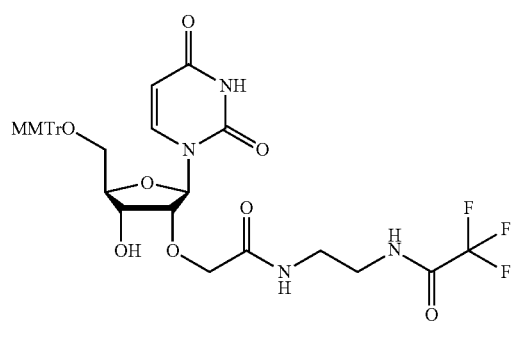

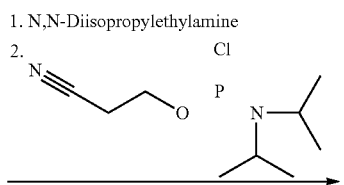

26

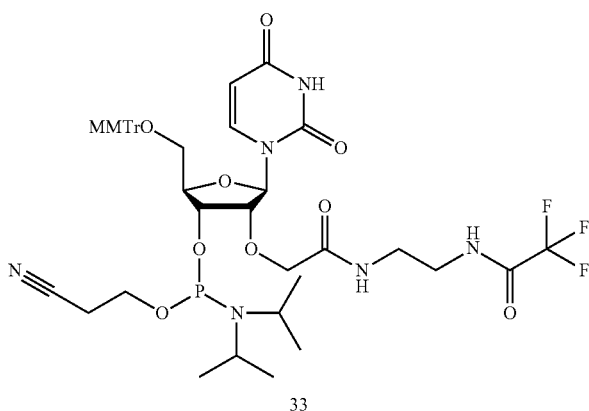

33

Example 13

Synthesis of 2'-O-AECM Modified Oligonucleotides Containing Various Nucleobases The oligonucleotides with SEQ ID NO 11 was synthesized on an Applied Biosystems 392 DNA/RNA synthesizer. Monomers 4, 31-33 for the solid-phase synthesis were dried in vacuo in the presence of $P_2O_5$ prior to use. Oligonucleotide was assembled on pre-loaded CPG cartridges using 2-cyanoethyl phosphoramidite chemistry in a 1.0 µmol scale using 5-benzylthio-1-H-tetrazole as activator and 5 min coupling time. For the detritylation step an extra round of 2 minute DCA treatment was used. After synthesis the CPG was transferred from the cartridge to a tightly sealed serum flask and treated with 2 ml ethylenediamine solution (20% in methanol) for 24 h at room temperature. The CPG-resin was then removed by filtration and washed with 4 ml methanol and 4 ml H₂O. The filtrate was evaporated under reduced pressure at 40° C., H₂O was added and the crude oligonucleotide product was lyophilized. The oligonucleotides were then purified with RP HPLC using an Discovery Bio Wide Pore C18-5 (250×4.6 mm, 5 μm) column at 50° C. First 100% buffer A was flushed through for 2 min, then a linear gradient of 0-25 buffer B over 45 min was used. Buffer A: 50 mM triethylammonium acetate in water (pH 6.5); Buffer B: 50 mM triethylammonium acetate (pH 6.5) in 50 aqueous acetonitrile. The oligonucleotide was lyophilized three times before use and stored frozen.

The invention claimed is:

1. A modified oligonucleotide of 5-50 nucleotide residues, wherein at least 25% of the nucleotides are independently modified at the 2' position to comprise the structure of formula I:

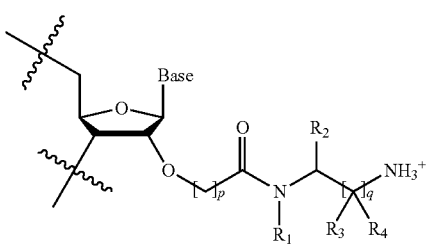

I wherein
Base is a purine or pyrimidine moiety;
$R^1$ and $R^2$ are independently selected from hydrogen and $C_1$-$C_3$ alkyl;
$R^3$ is selected from hydrogen and $C_1$-$C_6$ alkyl;
$R^4$ is selected from hydrogen and $C_1$-$C_{16}$ alkyl;
p=1 or 2; and
q=1 or 2.

2. The modified oligonucleotide according to claim 1, wherein at least 50% of the nucleotides of the oligonucleotide are independently modified at the 2' position to comprise the structure of formula I.

3. The modified oligonucleotide according to claim 2, wherein all of the nucleotides of the oligonucleotide are independently modified at the 2' position to comprise the structure of formula I.

4. The modified oligonucleotide according to claim 1, wherein $R^1$, $R^2$, $R^3$ and $R^4$ are independently selected from hydrogen and methyl.

5. The modified oligonucleotide according to claim 1, wherein $R^1$, $R^2$, $R^3$ and $R^4$ represent hydrogen.

6. The modified oligonucleotide according to claim 1, wherein p is 1.

7. The modified oligonucleotide according to claim 1, wherein q is 1.

8. The modified oligonucleotide according to claim 1, wherein said Base is selected from adenine, 2,6-diaminopurine, guanine, cytosine, 5-methylcytosine, uracil and thymine.

9. The modified oligonucleotide according to claim 1, wherein said modified nucleotides are independently modified at the 2' position to comprise a structure selected from:
2'-O-aminoethylcarbamoylmethyladenosine;
2'-O-aminoethylcarbamoylmethylcytidine;
2'-O-aminoethylcarbamoylmethyl-2-aminoadenosine;
2'-O-aminoethylcarbamoylmethylguanosine;
2'-O-aminoethylcarbamoylmethyl-5-methyluridine;
2'-O-aminoethylcarbamoylmethyluridine; and
2'-O-aminoethylcarbamoylmethyl-5-methylcytidine.

10. The modified oligonucleotide according to claim 9, wherein said modified nucleotides are modified at the 2' position to comprise the structure of 2'-O-aminoethylcarbamoylmethyladenosine.

11. The modified oligonucleotide according to claim 1, wherein the oligonucleotide comprises from 9 to 30 nucleotide residues.

12. The modified oligonucleotide according to claim 1, wherein the modified oligonucleotide comprises a further moiety selected from fatty acid and steroid derivatives, peptides, carbohydrates, drugs, reporter molecules, and nuclear localisation signals; and wherein said further moiety is conjugated with a non-modified nucleotide and/or with a modified nucleotide via another nucleotide moiety than with the 2' substituent of the modified structure of formula I.

13. A pharmaceutical composition comprising a modified oligonucleotide according to claim 1, together with a pharmaceutically acceptable carrier and/or excipient.

14. A method for treating, alleviating or preventing a disease, comprising administering to a patient in need thereof, a therapeutically effective amount of a modified oligonucleotide according to claim 1.

15. The modified oligonucleotide according to claim 1, wherein at least 80% of the nucleotides of the oligonucleotide are independently modified at the 2' position to comprise the structure of formula I.

* * * * *